(12) United States Patent
Volkmuth et al.

(10) Patent No.: US 9,834,766 B2
(45) Date of Patent: Dec. 5, 2017

(54) DNA BARCODES FOR MULTIPLEXED SEQUENCING

(75) Inventors: Wayne Volkmuth, Foster City, CA (US); Yann Chong Tan, Palo Alto, CA (US)

(73) Assignee: Atreca, Inc., San Carlos, CA (US)

( * ) Notice: Subject to any disclaimer, the term of this patent is extended or adjusted under 35 U.S.C. 154(b) by 303 days.

(21) Appl. No.: 14/342,048

(22) PCT Filed: Sep. 4, 2012

(86) PCT No.: PCT/US2012/053698
§ 371 (c)(1),
(2), (4) Date: Nov. 20, 2014

(87) PCT Pub. No.: WO2013/033721
PCT Pub. Date: Mar. 7, 2013

(65) Prior Publication Data
US 2015/0080266 A1 Mar. 19, 2015

Related U.S. Application Data

(60) Provisional application No. 61/530,676, filed on Sep. 2, 2011, provisional application No. 61/596,513, filed on Feb. 8, 2012.

(51) Int. Cl.
| | |
|---|---|
| *G01N 33/48* | (2006.01) |
| *C12N 15/10* | (2006.01) |
| *C12Q 1/68* | (2006.01) |
| *G06F 19/22* | (2011.01) |
| *G06F 19/18* | (2011.01) |
| *G06G 7/58* | (2006.01) |

(52) U.S. Cl.
CPC ..... *C12N 15/1089* (2013.01); *C12N 15/1065* (2013.01); *C12Q 1/6869* (2013.01); *C12Q 1/6876* (2013.01); *G06F 19/18* (2013.01); *G06F 19/22* (2013.01); *C12Q 2600/166* (2013.01)

(58) Field of Classification Search
CPC ...................................................... G06F 19/22
See application file for complete search history.

(56) References Cited

U.S. PATENT DOCUMENTS

| | | | | |
|---|---|---|---|---|
| 9,163,281 B2 * | 10/2015 | Porreca | ............... | C12Q 1/6869 |
| 2010/0323348 A1 | 12/2010 | Hamady et al. | | |
| 2011/0065589 A1 * | 3/2011 | Dattagupta | ............. | G06F 19/28 506/5 |
| 2011/0087439 A1 | 4/2011 | Ziegler et al. | | |

FOREIGN PATENT DOCUMENTS

WO 2012/148497 A2 11/2012

OTHER PUBLICATIONS

PCT/US12/53698, International Search Report and Written Opinion, dated Jan. 18, 2013, 16 pages.
Frank, Daniel. "*BARCRAWL* and *BARTAB*: software tools for the design and implementation of barcoded primers for highly multiplexed DNA sequencing," *BMC Bioinformatics* 2009, 10:362 (Oct. 29, 2009), 13 pages.
Lennon et al., "A Scalable, fully automated process for construction of sequence-ready barcoded libraries for 454," *Genome Biology* 2010, 11:R15 (Feb. 5, 2010), 9 pages.

* cited by examiner

*Primary Examiner* — Eric S Dejong
(74) *Attorney, Agent, or Firm* — Kilpatrick Townsend & Stockton LLP

(57) ABSTRACT

The present disclosure provides methods for optimizing barcode design for multiplex DNA sequencing. Also disclosed are DNA barcodes optimized for use with particular sequencing technologies.

19 Claims, 2 Drawing Sheets

SEQUENCE LISTING

```
<160> NUMBER OF SEQ ID NOS: 402

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
caacaacaac gaaggaaggg aac                                            23
```

```
<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
cgtatcgcct ccctcgcgcc atcag                                           25

<210> SEQ ID NO 3
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gcgacgtctg ctatctcagt gtgcagtc                                        28

<210> SEQ ID NO 4
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
agtcagcgtg agagtacgtg cgtgtcat                                        28

<210> SEQ ID NO 5
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
acgactgtga tctgtgagta catcacgc                                        28

<210> SEQ ID NO 6
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
gctatcgaca gtactatcac agtcagct                                        28

<210> SEQ ID NO 7
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
gcagtctcta tcgagcgtac tcagtaca                                        28

<210> SEQ ID NO 8
```

```
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
tagagtgtat cagctgactg cgtctatc                                              28

<210> SEQ ID NO 9
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
tctgcagacg tcgactctgc tgagtgac                                              28

<210> SEQ ID NO 10
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
acatctactc gacacactgt acagtagc                                              28

<210> SEQ ID NO 11
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
cgagtactac gtgtgactga tacactgc                                              28

<210> SEQ ID NO 12
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
actcgagtgt cgctgcacgt acgtacgt                                              28

<210> SEQ ID NO 13
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
gtgatcgacg tacagagtga tacgagct                                              28

<210> SEQ ID NO 14
<211> LENGTH: 28
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
cagtatcgct agcatactag tgcagata                                              28

<210> SEQ ID NO 15
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
acgtgctaca gagagtctgc tcagagca                                              28

<210> SEQ ID NO 16
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
gtcgagagca ctactacaga gtcgatca                                              28

<210> SEQ ID NO 17
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
gagagtctct acacacgata cgtagatc                                              28

<210> SEQ ID NO 18
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
cgtagtcaca gtgtagtcga gtcatcag                                              28

<210> SEQ ID NO 19
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
acacatcatc tacgtagcga gagagtac                                              28

<210> SEQ ID NO 20
<211> LENGTH: 28
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 20
actagatcgc tgcacgcata gatactag                                          28

<210> SEQ ID NO 21
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
atcactacgc atcgcatcag tatctacg                                          28

<210> SEQ ID NO 22
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
ctagtgtaga gtcacgagat ctcagcag                                          28

<210> SEQ ID NO 23
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
acacgtactc agtcatacag agcgagca                                          28

<210> SEQ ID NO 24
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
actcatagcg atacgtgtgc gtcatacg                                          28

<210> SEQ ID NO 25
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
gctctgtgtg tcgatactca gtctacta                                          28

<210> SEQ ID NO 26
<211> LENGTH: 28
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 26
ctgagacaga cgactagtac gagagcgt                                              28

<210> SEQ ID NO 27
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
cgacgatcac gagagcatct acacgtgc                                              28

<210> SEQ ID NO 28
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
atagagacta gagatagctc gcactgat                                              28

<210> SEQ ID NO 29
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
tactctctga gatacatcac gctcgacg                                              28

<210> SEQ ID NO 30
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
ctgtgtacgt gacgcactgc gagagatc                                              28

<210> SEQ ID NO 31
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
cacagtacta cacgtagctc gatcgact                                              28

<210> SEQ ID NO 32
<211> LENGTH: 28
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 32
acactgcata gagacactca catctcga                                              28

<210> SEQ ID NO 33
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
gcgagtgcgt gtatcgcaca gagtgtag                                              28

<210> SEQ ID NO 34
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
acgagacgag actgcgtcta cgctgcat                                              28

<210> SEQ ID NO 35
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
gtactagcgt atcactagag tgctgcgt                                              28

<210> SEQ ID NO 36
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
ctgtgatcag atcactcgat cagctgct                                              28

<210> SEQ ID NO 37
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
catctgagca catcgcatac gctacgta                                              28

<210> SEQ ID NO 38
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 38
gctgtctgcg tcgcagagta cgacagat                                28

<210> SEQ ID NO 39
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
gagagagatc gcacacacac tgctgcac                                28

<210> SEQ ID NO 40
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
gactgatcgc tgagacgtgc tgacgaga                                28

<210> SEQ ID NO 41
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
tagtctgtac actagagacg tacgcaga                                28

<210> SEQ ID NO 42
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
cgcatagcag tgagtcgata ctacgctc                                28

<210> SEQ ID NO 43
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
agagagtaca gcgacgagta gatcatca                                28

<210> SEQ ID NO 44
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 44
agcagagcac gtctatctgt actatctg                                          28

<210> SEQ ID NO 45
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
cgtatctcac agtactcaga tagcgtct                                          28

<210> SEQ ID NO 46
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
acatcagtgt gctgtgcgat cgacactg                                          28

<210> SEQ ID NO 47
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
gcacagcatc tcgctgtaga gtacgcta                                          28

<210> SEQ ID NO 48
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
gcgactagct gagcgatact gtagtgat                                          28

<210> SEQ ID NO 49
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
tacatctaga cgtgcgtgac actacaga                                          28

<210> SEQ ID NO 50
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 50
gtagtcatct gtgctcgatc actgagac                                      28

<210> SEQ ID NO 51
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
atagacacac atctgctcac tgtagctc                                      28

<210> SEQ ID NO 52
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
actgagcaga gcatcgacta gtgtcaga                                      28

<210> SEQ ID NO 53
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
tagagacacg tcagacacga gacagtag                                      28

<210> SEQ ID NO 54
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
agcgagcaga tagagcactg agtagtgc                                      28

<210> SEQ ID NO 55
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
gtctgatact catctatcgc agatagtc                                      28

<210> SEQ ID NO 56
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
```
tctacagcac gtactagcga ctcacgac                                         28

<210> SEQ ID NO 57
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
cgatagtcta tctagacgtc actcagtg                                         28

<210> SEQ ID NO 58
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
gacgatagca ctagctctgt gagctgac                                         28

<210> SEQ ID NO 59
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
tacgtacgag tgagtacgag tcgctagc                                         28

<210> SEQ ID NO 60
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
agtgcacgat acacacagtg tacgctat                                         28

<210> SEQ ID NO 61
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
cagcgagagc atctgtcagc atagtcac                                         28

<210> SEQ ID NO 62
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
ctactgtcat cactgctacg acgcatac                                          28

<210> SEQ ID NO 63
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
ctcacgctga tcagatagag actagcac                                          28

<210> SEQ ID NO 64
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
gactgcgagt cgacgagtac tacgtcta                                          28

<210> SEQ ID NO 65
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
tcgagtcaca gtacagtgtc tcgcagcg                                          28

<210> SEQ ID NO 66
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
tctgcgatag acgctacaca cgtcgaga                                          28

<210> SEQ ID NO 67
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
ctcacatagt agacgacagt cacgactg                                          28

<210> SEQ ID NO 68
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
gtagctcgca tacacgtgct gagtcgca                                          28

<210> SEQ ID NO 69
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
tcgctctctc acgatactgc gtctgagt                                          28

<210> SEQ ID NO 70
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
gagcatagta cgtgagtagc agtcagcg                                          28

<210> SEQ ID NO 71
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
gcagacatac gcactcgagt cgactacg                                          28

<210> SEQ ID NO 72
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
tcatcagtgt gtagcactag tcagtgtg                                          28

<210> SEQ ID NO 73
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
agcacagcta cgcagtacac tagatagc                                          28

<210> SEQ ID NO 74
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
tctgactaga gtcagagcgt ctacatct                                          28

```
<210> SEQ ID NO 75
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
tagcagtgag acatcgctag actgctac                                              28

<210> SEQ ID NO 76
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
tacacgatag agtctatcta gcagagag                                              28

<210> SEQ ID NO 77
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
cactgtgcgt gcgtgtatct gtcacgtc                                              28

<210> SEQ ID NO 78
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
cgtgactcta gctacgtcga gtagtcga                                              28

<210> SEQ ID NO 79
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
gtctagcact ctcacgctca tacagtga                                              28

<210> SEQ ID NO 80
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
ctagacgtgt gacgagtcac tatcgcac                                              28
```

```
<210> SEQ ID NO 81
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
tcgagcatac gtctagacac acgtcgct                                       28

<210> SEQ ID NO 82
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
ctatcgatcg agagctgacg catcagta                                       28

<210> SEQ ID NO 83
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
cgtgtctcag cgatctacgc tgtgctca                                       28

<210> SEQ ID NO 84
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
gtgctcatct atcagcgagt agcgactc                                       28

<210> SEQ ID NO 85
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
tctagagata ctgtgcagtc tgtctagc                                       28

<210> SEQ ID NO 86
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
gtgatcagat acatctactc tcagtcag                                       28

<210> SEQ ID NO 87
```

```
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
tctgcgtcag tgagatcacg ctgcagag                                          28

<210> SEQ ID NO 88
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
gagtgtagac gctacatcga gagtactg                                          28

<210> SEQ ID NO 89
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
gagactctgt gtgtgatcat cgagagta                                          28

<210> SEQ ID NO 90
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
tagtctcatc tctcatcaga gtgtgcat                                          28

<210> SEQ ID NO 91
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
gcgtgcgaga tagcatctcg agcatcat                                          28

<210> SEQ ID NO 92
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
cgtagcacgt ctctgacgct gagtgcta                                          28

<210> SEQ ID NO 93
<211> LENGTH: 28
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
tcacgctcac gtgctcagtg atcatact                                            28

<210> SEQ ID NO 94
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
gacactcact gtgcagatct acagctat                                            28

<210> SEQ ID NO 95
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
ctcgacatcg agtgcgtgtg tacgtctc                                            28

<210> SEQ ID NO 96
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
tcgctgctgc gatagcacga gagagaca                                            28

<210> SEQ ID NO 97
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
atactcagtc gacgatctct cgctgtgt                                            28

<210> SEQ ID NO 98
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
cagtagtaga gcacagatag cgtctcgc                                            28

<210> SEQ ID NO 99
<211> LENGTH: 28
<212> TYPE: DNA
```

<213> ORGANISM: Artificial Sequence
<220> FEATURE:
<223> OTHER INFORMATION: Description of Artificial Sequence: Synthetic
oligonucleotide

<400> SEQUENCE: 99
cactctactg tgagcagtag cacgtcac                                28

<210> SEQ ID NO 100
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 100
gtgtacatag cgtagatact gatcgaca                                28

<210> SEQ ID NO 101
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 101
cacatagtct gctgagtgta gcgtgtgc                                28

<210> SEQ ID NO 102
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 102
cagcgagtgt agtgacatac agagctgc                                28

<210> SEQ ID NO 103
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 103
tacacactcg cacatcgctg cgtgacga                                28

<210> SEQ ID NO 104
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 104
ctacagtcga gtcatcagtg cgtacgta                                28

<210> SEQ ID NO 105
<211> LENGTH: 28
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 105
gcgtcatcgc agtgtacacg catacagc                                       28

<210> SEQ ID NO 106
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
tagatcgctc tcacacgcac gacacgtc                                       28

<210> SEQ ID NO 107
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
ctatcgagag agcacgtgtg tctcgcta                                       28

<210> SEQ ID NO 108
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
agtcgatcga tagcacatcg ctcgcata                                       28

<210> SEQ ID NO 109
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
gtcacagtag agagtcgatc gagataca                                       28

<210> SEQ ID NO 110
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
cgacgtcaga tacactacag atcacatc                                       28

<210> SEQ ID NO 111
<211> LENGTH: 28
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 111
agtgctctgt agtcgacgat agcgtgcg                                            28

<210> SEQ ID NO 112
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
atcagcgaca gctgtacagt gtacactg                                            28

<210> SEQ ID NO 113
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
gcgacacacg acactcacac atacgtga                                            28

<210> SEQ ID NO 114
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
cgtgtgctca gcagcgacat catcgaga                                            28

<210> SEQ ID NO 115
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
gagcgacagc tgacgctcga gtatcact                                            28

<210> SEQ ID NO 116
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116
tctacgtacg atagcacgca cactactc                                            28

<210> SEQ ID NO 117
<211> LENGTH: 28
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 117
tcatacatac agtcacatca gagtacgc    28

<210> SEQ ID NO 118
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118
atctctgcgt cgacacgtga gcatacat    28

<210> SEQ ID NO 119
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119
tatctgacgc acgtgacgct gtcgatac    28

<210> SEQ ID NO 120
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120
agtcactcac gtagtcactg tctcagct    28

<210> SEQ ID NO 121
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121
tacgagacac acgcagcagt acatcacg    28

<210> SEQ ID NO 122
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122
atctgtgagc gtctcagtag cgtagtct    28

<210> SEQ ID NO 123
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 123
acacagacga cagcatagta ctgcgagt                                          28

<210> SEQ ID NO 124
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124
actgctctgc tgtacgagag catctgta                                          28

<210> SEQ ID NO 125
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125
gcacgtcacg acgtcataca tctacacg                                          28

<210> SEQ ID NO 126
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 126
gagcgagcat agctcagtct acgtacgc                                          28

<210> SEQ ID NO 127
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127
gtgatcacga gtgagacacg ctgcgtgt                                          28

<210> SEQ ID NO 128
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 128
agtctcagcg agtctgagcg acgtgagt                                          28

<210> SEQ ID NO 129
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 129
gagtgtgcta gagcgagata gcagcgtc                                              28

<210> SEQ ID NO 130
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 130
cagtgacgta gtgtcgagac gtgagtat                                              28

<210> SEQ ID NO 131
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 131
tctcactatc tagacgatcg agctgtat                                              28

<210> SEQ ID NO 132
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132
ctgcgagaga tcagacgtga cacagacg                                              28

<210> SEQ ID NO 133
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133
tcgctacgca cacagtgagt ctatctga                                              28

<210> SEQ ID NO 134
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 134
cgtgtatcac gtcgcacgta ctcgacac                                              28

<210> SEQ ID NO 135
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135
```
tagtcgagta gacagcgtgt agtcatag                                28

<210> SEQ ID NO 136
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 136
gtcatagcgt gtctcagcac gactagac                                28

<210> SEQ ID NO 137
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 137
agctgtagac tatctatctg tgagacga                                28

<210> SEQ ID NO 138
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 138
acgcagacag cactagcatc tctatcgc                                28

<210> SEQ ID NO 139
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139
cgtgtgtgta gtgatctatc tctagtac                                28

<210> SEQ ID NO 140
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 140
gctctagatc gcatctgtgt gctgtcga                                28

<210> SEQ ID NO 141
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141
gcgagtgtga cgtgtctgat actgatag                                     28

<210> SEQ ID NO 142
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 142
tatcagtgat ctctgacgct acacagat                                     28

<210> SEQ ID NO 143
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 143
ctcgcacatc atcatcacac tctgcagc                                     28

<210> SEQ ID NO 144
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 144
gtgcagtgtg tcacgacgtc atagtgct                                     28

<210> SEQ ID NO 145
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 145
cactcactct atcgactcat acatcagt                                     28

<210> SEQ ID NO 146
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 146
acgtacagtc actctgtcga tcgagcgt                                     28

<210> SEQ ID NO 147
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 147
cgcatctagc acgcagcacg cactatca                                     28

```
<210> SEQ ID NO 148
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 148
gacatactga gcgtacacac tagtactg                                              28

<210> SEQ ID NO 149
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 149
tcatagacag tcgagtgcag cacatcat                                              28

<210> SEQ ID NO 150
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 150
agacgagcgt gtagatagac tatcacat                                              28

<210> SEQ ID NO 151
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 151
gtagtatcag atacgtgtcg acgctatc                                              28

<210> SEQ ID NO 152
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 152
tagacacacg ctgtgtgcga tacacact                                              28

<210> SEQ ID NO 153
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 153
acgcacacag agagtgacac gagcagag                                              28
```

<210> SEQ ID NO 154
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 154
agagatagtc gatcagatct acacagct                                          28

<210> SEQ ID NO 155
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 155
actgcgatcg acgtgagtcg agacacac                                          28

<210> SEQ ID NO 156
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 156
gtatctctgt cactgtacat acacgagc                                          28

<210> SEQ ID NO 157
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 157
gtgtatcgct gtcgatcaga gcgagtag                                          28

<210> SEQ ID NO 158
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 158
atcatctgtc tgcgacgctc tagtcagc                                          28

<210> SEQ ID NO 159
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 159
gtgtctgatc gctgtcagat cgcatcga                                          28

```
<210> SEQ ID NO 160
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 160
gtatcgctct gctacgacta gctatcta                                         28

<210> SEQ ID NO 161
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 161
gatagcagca cgctcacgag tctagcga                                         28

<210> SEQ ID NO 162
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 162
gcagtgatac tcagcgtgag cacgtagc                                         28

<210> SEQ ID NO 163
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 163
cgatagatcg actgcgatca tagagcga                                         28

<210> SEQ ID NO 164
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 164
atcagtacgc tcagagcgtg tgcgagct                                         28

<210> SEQ ID NO 165
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 165
gagtctagtg ctagtgcgac agacgacg                                         28

<210> SEQ ID NO 166
```

```
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 166
cagcagcata catcatagcg tatcatca                                             28

<210> SEQ ID NO 167
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 167
atacagatca tacgacgtgt gctgtcta                                             28

<210> SEQ ID NO 168
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 168
cgatagtgtg cgtacactga gtactatc                                             28

<210> SEQ ID NO 169
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 169
catctagtga ctacacatac gacacacg                                             28

<210> SEQ ID NO 170
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 170
atctcatacg agcgtcagtg tatcgagc                                             28

<210> SEQ ID NO 171
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 171
tagtgtgcta cgatcagtct ctcgctgt                                             28

<210> SEQ ID NO 172
<211> LENGTH: 28
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 172
gtgcatctag catagacatc tagcatac                                         28

<210> SEQ ID NO 173
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 173
cgtgcatagc atagtgtaca gacacgta                                         28

<210> SEQ ID NO 174
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 174
tctgacatct acagtgctct cagcgaga                                         28

<210> SEQ ID NO 175
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 175
tagagtgctg tctgtatcac actacgca                                         28

<210> SEQ ID NO 176
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 176
tatctgcaga tcacagatca cgtactac                                         28

<210> SEQ ID NO 177
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 177
atactagcgt agactgcata ctagacag                                         28

<210> SEQ ID NO 178
<211> LENGTH: 28
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 178
ctacgtctcg acgacacgca gagtcgat                                          28

<210> SEQ ID NO 179
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 179
acatacgctg tacgtactgc gtgtactc                                          28

<210> SEQ ID NO 180
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 180
agagagtgta tctcagtgtg agtagcat                                          28

<210> SEQ ID NO 181
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 181
agatagtagt gcagcgtacg tgtcgata                                          28

<210> SEQ ID NO 182
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 182
cagcagctga gtatctctat catctagt                                          28

<210> SEQ ID NO 183
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 183
ctagtcgatc tgacactagt ctgtacac                                          28

<210> SEQ ID NO 184
<211> LENGTH: 28
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 184
gtgcgtagcg acagtgctga ctgtagac                                        28

<210> SEQ ID NO 185
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 185
cagagtagtc tgacgtagat ctgcgatc                                        28

<210> SEQ ID NO 186
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 186
tacatagtgc atacgagaca cactgcac                                        28

<210> SEQ ID NO 187
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 187
ctctgctact gctacgtgta gacagtat                                        28

<210> SEQ ID NO 188
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 188
agtgtgtgta tcgagtacgt ctgacacg                                        28

<210> SEQ ID NO 189
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 189
tcgatctgtc gagagtatct catcgctg                                        28

<210> SEQ ID NO 190
<211> LENGTH: 28
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 190
agcgtctgta cagatagcat cgatcagt                                              28

<210> SEQ ID NO 191
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 191
tagtacatca gcgactgctg cgactgca                                              28

<210> SEQ ID NO 192
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 192
cactcagcat actcgacaga tctgtgag                                              28

<210> SEQ ID NO 193
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 193
cacgcagcgt agcgtagtgt agactacg                                              28

<210> SEQ ID NO 194
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 194
agatacagtc tactagagag tgctgacg                                              28

<210> SEQ ID NO 195
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 195
tctcagcgac acgatcacgt cgagagtc                                              28

<210> SEQ ID NO 196
<211> LENGTH: 28
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 196
tcagatctcg cagacataca gcatcgca                28

<210> SEQ ID NO 197
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 197
cgctctcata gatagagcga gtcgcaga                28

<210> SEQ ID NO 198
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 198
ctgtctgcac gcatcgagtg tagtctat                28

<210> SEQ ID NO 199
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 199
gctacactat ctctacgcac tatctagt                28

<210> SEQ ID NO 200
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 200
agagctgcga tcgagtacat agagctat                28

<210> SEQ ID NO 201
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 201
ctgagcacta cgcacgactc tctgtgtc                28

<210> SEQ ID NO 202
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 202
gtgtgcgagc atctacacga cgtgctgt                                              28

<210> SEQ ID NO 203
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 203
agcatctctg tagagacaca gtgcgtca                                              28

<210> SEQ ID NO 204
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 204
ctagagctct cgagtgcact gactgacg                                              28

<210> SEQ ID NO 205
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 205
gatcacgtca tcgatcatct gtacgtca                                              28

<210> SEQ ID NO 206
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 206
acatcgcaca ctacagcaca tcgacata                                              28

<210> SEQ ID NO 207
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 207
agcactatct ctgtatcaca cgcagcgt                                              28

<210> SEQ ID NO 208
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 208
ctgactactc tgtgatcgct agacatag                                          28

<210> SEQ ID NO 209
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 209
gtgagacgag tgctgcgagt gatagtca                                          28

<210> SEQ ID NO 210
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 210
agtgatactg agagcgtacg tcgatcgc                                          28

<210> SEQ ID NO 211
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 211
atagtacacg tgtgtgagtg ctgtgatc                                          28

<210> SEQ ID NO 212
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 212
gtgctgcacg tagtgtacgt gtgtacgt                                          28

<210> SEQ ID NO 213
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 213
atagctctgc gacagcacag tgtgcgtg                                          28

<210> SEQ ID NO 214
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 214
```
cgtctgtgtg agctacgctc tgtgtgtg        28

<210> SEQ ID NO 215
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 215
cagactgaca cgagatagca cagagatc        28

<210> SEQ ID NO 216
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 216
gtacgtgtct catactacac atcacgtg        28

<210> SEQ ID NO 217
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 217
tcgatcatct gtactactct cgacatac        28

<210> SEQ ID NO 218
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 218
agagcgactg ctgctctgag cgtagata        28

<210> SEQ ID NO 219
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 219
agtcgacagc gtgtcatact atctagtg        28

<210> SEQ ID NO 220
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 220
gacgcacaga cgatctgtct agtcagtc                                28

<210> SEQ ID NO 221
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 221
tacagcgtgt gagagcgata gagagtct                                28

<210> SEQ ID NO 222
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 222
gtgatctagc gtgtgtgtgc atagcacg                                28

<210> SEQ ID NO 223
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 223
tacacagacg agagagctca catacgct                                28

<210> SEQ ID NO 224
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 224
atcacgcaga gctcgctctg acagcgta                                28

<210> SEQ ID NO 225
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 225
tcacgtacac actctgtgct gagatctg                                28

<210> SEQ ID NO 226
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 226
gatacagtga ctacgtcagt ctcagtac                                28

<210> SEQ ID NO 227
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 227
gacacgtgtc atagagtcta gatcactc                                          28

<210> SEQ ID NO 228
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 228
agctatcaca tagctgagca gacgatct                                          28

<210> SEQ ID NO 229
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 229
agtagataca gagcagcagc tatctact                                          28

<210> SEQ ID NO 230
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 230
ctgcgtctgt gctgtctaga gagagcta                                          28

<210> SEQ ID NO 231
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 231
acgatcacga tcgctgcgta gtgacgtg                                          28

<210> SEQ ID NO 232
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 232
gatacagact ctagcgacgc agtacact                                          28

<210> SEQ ID NO 233
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 233
gcgtcgcacg agtatcgatc tgctcatc                                          28

<210> SEQ ID NO 234
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 234
agctcgacta cgacgctagc atcgctac                                          28

<210> SEQ ID NO 235
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 235
catcatacac gtgatagaga ctgcacgt                                          28

<210> SEQ ID NO 236
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 236
tacactcata gactcacgca gtagcatc                                          28

<210> SEQ ID NO 237
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 237
tcagtgagtc gatcgagctg atcgagtc                                          28

<210> SEQ ID NO 238
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 238
cgtgtgagac tagtgtgtac atagagtg                                          28

```
<210> SEQ ID NO 239
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 239
agctagtaca gtctacactg cacgctca                                          28

<210> SEQ ID NO 240
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 240
actagctcag agctagctga tcacgtgt                                          28

<210> SEQ ID NO 241
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 241
gtgtgtcacg agactagaga gactctgc                                          28

<210> SEQ ID NO 242
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 242
ctcgctgact ctgctgcata catcacta                                          28

<210> SEQ ID NO 243
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 243
gtgtgctctc atcacgctct gtgagact                                          28

<210> SEQ ID NO 244
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 244
tatctcgact cagcagtgca cagagtgt                                          28

<210> SEQ ID NO 245
```

```
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 245
gcacagtcat ctgcagcaca cgtgtcag                                          28

<210> SEQ ID NO 246
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 246
acagacactc tagctgacag ctcagaga                                          28

<210> SEQ ID NO 247
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 247
cgcagacagc tcatcgacga cacacata                                          28

<210> SEQ ID NO 248
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 248
catagtgatc gagagtgtgt gacactgt                                          28

<210> SEQ ID NO 249
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 249
ctgagcgtga ctgtcacatc gactgtga                                          28

<210> SEQ ID NO 250
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 250
tactagcact ctgtacgtac gctagctg                                          28

<210> SEQ ID NO 251
<211> LENGTH: 28
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 251
ctctgcatag tactctgtgt ctgcacac                                             28

<210> SEQ ID NO 252
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 252
atagcgtcta cgctgagact cgctcata                                             28

<210> SEQ ID NO 253
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 253
cagagactcg agctgacgta ctctctct                                             28

<210> SEQ ID NO 254
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 254
gactctctac atctcagaca tctgtgtc                                             28

<210> SEQ ID NO 255
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 255
agactgcagt actagcacga tcgctagt                                             28

<210> SEQ ID NO 256
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 256
tctgtcacgc tagtctagta ctgactca                                             28

<210> SEQ ID NO 257
<211> LENGTH: 28
<212> TYPE: DNA
```

-continued

```
<213> ORGANISM: Artificial Sequence
<220> FEATURE:
<223> OTHER INFORMATION: Description of Artificial Sequence: Synthetic
      oligonucleotide

<400> SEQUENCE: 257
cacgtagcag tcacgtacac gcacgtgt                                              28

<210> SEQ ID NO 258
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 258
cagcagtgat ctcgacacgc tgtgacta                                              28

<210> SEQ ID NO 259
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 259
actagcgtac gtgcatagtg tagagcga                                              28

<210> SEQ ID NO 260
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 260
gatagtgctg cagctctgca tcgctctg                                              28

<210> SEQ ID NO 261
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 261
ctgtcgctac tgtgactaca gcagcacg                                              28

<210> SEQ ID NO 262
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 262
cgtctgagtc atctcgacgt gagcatac                                              28

<210> SEQ ID NO 263
<211> LENGTH: 28
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 263
agtcatactc gctgactact ctgtgagt                                          28

<210> SEQ ID NO 264
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 264
gcagtacatc tgagtacgca tacatcac                                          28

<210> SEQ ID NO 265
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 265
cgtacgtact gctcgcagct actacgag                                          28

<210> SEQ ID NO 266
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 266
agatacgtgc actgtctcag agacagct                                          28

<210> SEQ ID NO 267
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 267
gtcgctagtc actgatctag cgacgcag                                          28

<210> SEQ ID NO 268
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 268
agtgtctagt agactcagta ctctcgac                                          28

<210> SEQ ID NO 269
<211> LENGTH: 28
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 269
tatcactgac agcagcagta tcgcagac                                           28

<210> SEQ ID NO 270
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 270
catcgctaca cgactgtagc actctctg                                           28

<210> SEQ ID NO 271
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 271
gagcagcgag atacacgcat ctgctcga                                           28

<210> SEQ ID NO 272
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 272
tacagctctc agtgtgtgtc agtagcgt                                           28

<210> SEQ ID NO 273
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 273
gagtcatcag cagagtgaca gtgtctat                                           28

<210> SEQ ID NO 274
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 274
agctgactgt gagtatctcg cagatctc                                           28

<210> SEQ ID NO 275
<211> LENGTH: 28
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 275
agtatctact ctgagtgacg agtagagc                                          28

<210> SEQ ID NO 276
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 276
gcatactgta tcatctcatc tactgcac                                          28

<210> SEQ ID NO 277
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 277
gagactactc acatctcacg tgatagag                                          28

<210> SEQ ID NO 278
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 278
tcgctctgag tgatctgcac tacgatct                                          28

<210> SEQ ID NO 279
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 279
agagtgcgtg cgtcacacag ctcagagt                                          28

<210> SEQ ID NO 280
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 280
ctgtctacac tactactctg cacacgag                                          28

<210> SEQ ID NO 281
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 281
tctagcatag tgactgacgt gagcatca                                              28

<210> SEQ ID NO 282
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 282
tacgtgctca gatctctcag tcgacaga                                              28

<210> SEQ ID NO 283
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 283
catacagctg agatcagtag acgagctg                                              28

<210> SEQ ID NO 284
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 284
agactctact ctcactctct gagtgctg                                              28

<210> SEQ ID NO 285
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 285
actagactga gtgtgtactc acgcatac                                              28

<210> SEQ ID NO 286
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 286
cactcacagc tgctatcagc tacgtaca                                              28

<210> SEQ ID NO 287
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 287
tactactact gctgtgtcta tctgcacg                                           28

<210> SEQ ID NO 288
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 288
agcacgagcg tctgagatct ctgcagta                                           28

<210> SEQ ID NO 289
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 289
cgtctctgtc gacgagagct gatagtat                                           28

<210> SEQ ID NO 290
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 290
gtgcacgtga gtagtgtagc tgagactg                                           28

<210> SEQ ID NO 291
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 291
acgatacgtc gcatacactc atcagtca                                           28

<210> SEQ ID NO 292
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 292
gtacgactct gcgtagctgt gtgctcat                                           28

<210> SEQ ID NO 293
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 293
tcactgtgct acgtctcagc acagacga 28

<210> SEQ ID NO 294
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 294
cagatctgct gatctgatct gcacgtag 28

<210> SEQ ID NO 295
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 295
actgtgactg cagatagagt cgcagcag 28

<210> SEQ ID NO 296
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 296
atactgactc tatcacatac tcagacgc 28

<210> SEQ ID NO 297
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 297
tcgcagtact gcagcagaga gatacgtc 28

<210> SEQ ID NO 298
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 298
gtctagagtg catagactgc tacacagc 28

<210> SEQ ID NO 299
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 299
tctgtgcagt cagactgctg atctctag                                28

<210> SEQ ID NO 300
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 300
cagctgcgtg tagatctgag tgctagcg                                28

<210> SEQ ID NO 301
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 301
actcgctctg ctctgctgta ctgatcag                                28

<210> SEQ ID NO 302
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 302
tagtactatc acagctctga cagcacag                                28

<210> SEQ ID NO 303
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 303
agctgtgcat ctgcgtgtgc gagtgtga                                28

<210> SEQ ID NO 304
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 304
tcgactgact ctcatagagc tagctgtg                                28

<210> SEQ ID NO 305
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 305
gtagcagacg agacacatca gtgacagt                                28

```
<210> SEQ ID NO 306
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 306
catcgacgca tagcgatcga tagctctg                                              28

<210> SEQ ID NO 307
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 307
gatactcact agtcacgtgc agtgctga                                              28

<210> SEQ ID NO 308
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 308
cacatcagac gctcacagag agactcta                                              28

<210> SEQ ID NO 309
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 309
acgtgtgcga cacgagacgt gtagtaca                                              28

<210> SEQ ID NO 310
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 310
cgctgatacg tcactagtct gactcaga                                              28

<210> SEQ ID NO 311
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 311
actgactgca tacgtacgta ctgagtgt                                              28
```

<210> SEQ ID NO 312
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 312
ctgcacagta tcgcatagct gtgtgtag                                              28

<210> SEQ ID NO 313
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 313
gcgagctctc atctcgacag agactcac                                              28

<210> SEQ ID NO 314
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 314
tcactagtag ctcatactac tagagcac                                              28

<210> SEQ ID NO 315
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 315
catacgtgca tctgacgaga tagtgtgc                                              28

<210> SEQ ID NO 316
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 316
cgctgcgtct gactcacatc acactact                                              28

<210> SEQ ID NO 317
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 317
atagtgtgag actcgatcgc atcacatc                                              28

```
<210> SEQ ID NO 318
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 318
agtatcgcta cagagatctc atctgtag                                              28

<210> SEQ ID NO 319
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 319
gtagatacgt ctcgctagtc acagcata                                              28

<210> SEQ ID NO 320
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 320
tagcgtgtcg ctactgcacg tgctcact                                              28

<210> SEQ ID NO 321
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 321
cgcactgctg cgtagtagtg ctctctag                                              28

<210> SEQ ID NO 322
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 322
agcagtcgct gagcgtacac tcactgtc                                              28

<210> SEQ ID NO 323
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 323
gacacgctag tctgtctctg tgacatag                                              28

<210> SEQ ID NO 324
```

```
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 324
actctcactg tacgtgtgtg tactctgc                                          28

<210> SEQ ID NO 325
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 325
gtgagctcta tcatagtctc gctgctca                                          28

<210> SEQ ID NO 326
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 326
cactgtgaca ctgtagctgc agagtgca                                          28

<210> SEQ ID NO 327
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 327
cgcatacact gtctgtgtac tcgctgta                                          28

<210> SEQ ID NO 328
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 328
tcgagtgcga gctctacgca tacgagac                                          28

<210> SEQ ID NO 329
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 329
atctctgtga gctgagtgag atactgcg                                          28

<210> SEQ ID NO 330
<211> LENGTH: 28
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 330
cgagctgtat cagcagagtc tcgagata                                        28

<210> SEQ ID NO 331
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 331
gagatagacg ctgtacgtgt ctcatagc                                        28

<210> SEQ ID NO 332
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 332
gatagcgtag tgtctagctc agcgtctc                                        28

<210> SEQ ID NO 333
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 333
atctgacgtg actgatagtc atacgtgt                                        28

<210> SEQ ID NO 334
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 334
cgtagagcac agtgtactct ctgagact                                        28

<210> SEQ ID NO 335
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 335
atctcagtct ctcgctagtc tctcactg                                        28

<210> SEQ ID NO 336
<211> LENGTH: 28
<212> TYPE: DNA
```

<213> ORGANISM: Artificial Sequence
<220> FEATURE:
<223> OTHER INFORMATION: Description of Artificial Sequence: Synthetic oligonucleotide

<400> SEQUENCE: 336
gtgcgtgagt agactctcac gcactgta        28

<210> SEQ ID NO 337
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 337
gtgctactag cactatctag catagtgt        28

<210> SEQ ID NO 338
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 338
gtcacgtcag actgctatca cgtgctct        28

<210> SEQ ID NO 339
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 339
gctctcagag tgtagtctgt gagagctc        28

<210> SEQ ID NO 340
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 340
cagtgcgact cacactcaga gcgtctct        28

<210> SEQ ID NO 341
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 341
gagtgagctg tgtgacagcg tctgtaca        28

<210> SEQ ID NO 342
<211> LENGTH: 28
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 342
tctcgagcgt ctgtatcgca gcatctgc                                          28

<210> SEQ ID NO 343
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 343
gcatcgcagt atcagagctg cgactgtg                                          28

<210> SEQ ID NO 344
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 344
gtagagagat acagtctact agatcgct                                          28

<210> SEQ ID NO 345
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 345
acactcgagt gcactacagc tgtctgca                                          28

<210> SEQ ID NO 346
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 346
acatacacga tagcgtatct cactctca                                          28

<210> SEQ ID NO 347
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 347
ctgagcgtct agctcatcac atagcacg                                          28

<210> SEQ ID NO 348
<211> LENGTH: 28
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 348
gacgatctag agtctgcata gtagctat                                         28

<210> SEQ ID NO 349
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 349
ctcacgtatc tgtagacgtg agtagaga                                         28

<210> SEQ ID NO 350
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 350
ctctctacag agtcgactca ctctagcg                                         28

<210> SEQ ID NO 351
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 351
gatacacata gctgctgata gagtgtca                                         28

<210> SEQ ID NO 352
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 352
atacgagaga gtactctcgc tgctatct                                         28

<210> SEQ ID NO 353
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 353
tcgatcgctg cagtgcgaga ctctactc                                         28

<210> SEQ ID NO 354
<211> LENGTH: 28
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 354
ctacactctc atactgtgag cagactga                                              28

<210> SEQ ID NO 355
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 355
ctcactcgca gctacgagct ctcagtga                                              28

<210> SEQ ID NO 356
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 356
gtcagtagtg ctgtacgtag tgactcga                                              28

<210> SEQ ID NO 357
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 357
gagcgtctcg atctgtgacg ctgtctag                                              28

<210> SEQ ID NO 358
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 358
gctgcataca cagctcgcta tctcgcac                                              28

<210> SEQ ID NO 359
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 359
gcgagcacat cagtgataca tcagatag                                              28

<210> SEQ ID NO 360
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 360
gatcatcgag tactgctgta tcagacat                                28

<210> SEQ ID NO 361
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 361
tagactcaca gagacgagta cgtctgtg                                28

<210> SEQ ID NO 362
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 362
acacgtgtcg actcgactgt gctctgat                                28

<210> SEQ ID NO 363
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 363
ctctgtagag cgagtatcat agtcatag                                28

<210> SEQ ID NO 364
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 364
gactagcgag ctgtgctcta ctctctga                                28

<210> SEQ ID NO 365
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 365
tcgctgcgtc tatctgtgtg acagctca                                28

<210> SEQ ID NO 366
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 366
gtagtgtcac gcactctctg acatagta                                          28

<210> SEQ ID NO 367
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 367
cgagagagca gctctgagta cgtgtact                                          28

<210> SEQ ID NO 368
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 368
gactgagacg agcactgtgc gtagcatc                                          28

<210> SEQ ID NO 369
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 369
tcgctgtaga cgcagtgaca gtgcagct                                          28

<210> SEQ ID NO 370
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 370
cgctgtagtc tacacagcgt gtgtagtc                                          28

<210> SEQ ID NO 371
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 371
gactgctgta tcgctcatca gcgataca                                          28

<210> SEQ ID NO 372
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 372
```
gctgtgtgca ctctgcatac agtgcgac                                        28

<210> SEQ ID NO 373
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 373
tatcacgagc agtctcagtg ctgatcgc                                        28

<210> SEQ ID NO 374
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 374
tagtgagatc tcgcatagtg agcgagcg                                        28

<210> SEQ ID NO 375
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 375
tacgtacgat catacatacg tgtgtgag                                        28

<210> SEQ ID NO 376
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 376
acgacgcata ctactgtcac gcactcac                                        28

<210> SEQ ID NO 377
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 377
actgtatcta gtacgtgcac acgctcag                                        28

<210> SEQ ID NO 378
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 378

```
gtgtgacgtg ctctacgtag ctctgctc                                          28
```

<210> SEQ ID NO 379
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 379

```
cgacactgag tgctacagct catcacgt                                          28
```

<210> SEQ ID NO 380
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 380

```
ctgcatcatc tcagagagca tacactag                                          28
```

<210> SEQ ID NO 381
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 381

```
agcgagtacg ctagtgtctc acatcgca                                          28
```

<210> SEQ ID NO 382
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 382

```
ctgatactgt gtctctctgc tgatctga                                          28
```

<210> SEQ ID NO 383
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 383

```
agctagtgtg tagcagctct catacaga                                          28
```

<210> SEQ ID NO 384
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 384

```
tctctcgaga cgagagatag agacgtga                                          28
```

<210> SEQ ID NO 385
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 385
gagagactgt gtagtgtaga gcacagac                                       28

<210> SEQ ID NO 386
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 386
agtgtcatca gtcgcagcat cactctgt                                       28

<210> SEQ ID NO 387
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 387
gatagagcac gcagtagtag tatctgtg                                       28

<210> SEQ ID NO 388
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 388
atagcacgca gacgagatca cgcagact                                       28

<210> SEQ ID NO 389
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 389
cgtgtgtact cagtgtcata ctgcacat                                       28

<210> SEQ ID NO 390
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 390
acactcgcat cagtcagagt gatagtct                                       28

<210> SEQ ID NO 391
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 391
gcatactaga gctctctgac atctacat                                          28

<210> SEQ ID NO 392
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 392
tatcgcacag tgcgtactcg atctgaca                                          28

<210> SEQ ID NO 393
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 393
tcatctactc tgcgagagtc gctctact                                          28

<210> SEQ ID NO 394
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 394
tctacgtgtg tgcgactcta ctcatagt                                          28

<210> SEQ ID NO 395
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 395
gcagatagag agacgcatac tctgtcta                                          28

<210> SEQ ID NO 396
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 396
agcagctcga gatactagtg agcagcac                                          28

<210> SEQ ID NO 397
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 397
cgtgtgcgtc tgtgatagta cagtctct                                            28

<210> SEQ ID NO 398
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 398
tagtgtgcag tacacgctat cagtatca                                            28

<210> SEQ ID NO 399
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 399
cgcacatcac gagagtgtgc tgtgtaca                                            28

<210> SEQ ID NO 400
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 400
gcgtcatagc tgctcgagag tctgagca                                            28

<210> SEQ ID NO 401
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 401
gctcagagca gacgatctgt ctcacgct                                            28

<210> SEQ ID NO 402
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 402
tatcgacaca gcacagagag agagacac                                            28

DNA BARCODES FOR MULTIPLEXED SEQUENCING

CROSS REFERENCE TO RELATED APPLICATIONS

This application claims the benefit of U.S. Provisional Application No. 61/530,676, filed Sep. 2, 2011, and U.S. Provisional Application No. 61/596,513, filed Feb. 8, 2012, which are hereby incorporated by reference in their entireties for all purposes.

BACKGROUND

Multiplex processing of DNA samples using oligonucleotide "barcode" tags can make sample processing more efficient. In this approach, a number of distinct oligonucleotides are selected, and for each DNA sample a unique olignucleotide is incorporated (e.g. by including it in a vector during cloning or as part of a PCR primer during amplification). The number of samples that can be processed in parallel is determined by how reliably the barcode tags can be identified from the resulting DNA sequences. There are $4^N$ oligonucleotides of length N, but because of sequencing errors it is not possible to reliably distinguish $4^N$ oligonucleotide sequences with 100% probability. Thus, better methods for optimizing the design of the barcode sequences for particular sequencing technologies, which take into account particular estimated sets of errors are needed. The present invention satisfies these and other needs.

SUMMARY

The present disclosure provides methods for optimizing barcode design for multiplex DNA sequencing and optimized DNA barcodes.

In a first aspect, the present invention provides a computer-implemented method for determining an estimated misidentification error rate of a plurality of barcodes, comprising: obtaining a first dataset, wherein the first dataset comprises data associated with the plurality of barcodes, wherein the barcodes are selected to minimize the alignment score of each barcode relative to the other barcodes in the plurality of barcodes, wherein the alignment score is determined by choosing a scoring matrix and performing a global alignment of the first barcode with the second barcode, and determining, by a computer processor, the estimated misidentification error rates of the plurality of barcodes by performing simulated sequencing reads for each barcode and calculating, for each barcode, the fraction of simulated reads for which one or more other barcodes in the plurality of barcodes has alignment score greater than or equal to that for the barcode from which the simulated read was generated.

In a second aspect, the present invention provides a computer-implemented method for determining an estimated misidentification error rate of a plurality of barcodes, comprising: obtaining a first dataset, wherein the first dataset comprises data associated with the plurality of barcodes, wherein the barcodes are selected to maximize the edit distance of each barcode relative to the other barcodes in the plurality of barcodes, and determining, by a computer processor, the estimated misidentification error rates of the plurality of barcodes by performing simulated sequencing reads for each barcode and calculating, for each barcode, the fraction of simulated reads for which one or more other barcodes in the plurality of barcodes has edit distance less than or equal to that for the barcode from which the simulated read was generated.

In a third aspect, the present invention provides a computer-implemented method for selecting a plurality of barcodes, comprising: obtaining a first dataset, wherein the first dataset comprises data associated with the plurality of barcodes, wherein the barcodes are selected to maximize the edit distance of each barcode relative to the other barcodes in the plurality of barcodes, wherein the edit distance is the total number of mismatches and gaps that exist along the length of a first barcode and a second barcode upon global alignment of the first barcode and the second barcode, and determining, by a computer processor, the estimated misidentification error rates of the plurality of barcodes by performing simulated sequencing reads for each barcode and calculating, for each barcode, the fraction of simulated reads for which one or more other barcodes in the plurality of barcodes has edit distance less than or equal to that for the barcode from which the read was generated, and selecting the plurality of barcodes for use in labeling one or more samples, wherein the selection is based upon the determined, estimated misidentification error rate of the plurality of barcodes being less than a desired worst-case misidentification error rate.

In a fourth aspect, the present invention provides a system for determining an estimated misidentification error rate of a plurality of barcodes, the system comprising: a storage memory for storing a dataset associated with the plurality of barcodes, wherein the barcodes are selected to minimize the alignment score of each barcode relative to the other barcodes in the plurality of barcodes, wherein the alignment score is determined by choosing a scoring matrix and performing a global alignment of the first barcode with the second barcode, and a processor communicatively coupled to the storage memory for determining, by a computer processor, the estimated misidentification error rates of the plurality of barcodes by performing simulated sequencing reads for each barcode and calculating, for each barcode, the fraction of simulated reads for which one or more other barcodes in the plurality of barcodes has alignment score greater than or equal to that for the barcode from which the simulated read was generated.

In a fifth aspect, the present invention provides a computer-readable storage medium storing computer-executable program code, the program code comprising: program code for storing a dataset associated with the plurality of barcodes, wherein the barcodes are selected to minimize the alignment score of each barcode relative to the other barcodes in the plurality of barcodes, wherein the alignment score is determined by choosing a scoring matrix and performing a global alignment of the first barcode with the second barcode, and program code for determining the estimated misidentification error rates of the plurality of barcodes by performing simulated sequencing reads for each barcode and calculating, for each barcode, the fraction of simulated reads for which one or more other barcodes in the plurality of barcodes has alignment score greater than or equal to that for the barcode from which the simulated read was generated.

In a sixth aspect, the present invention provides a system for determining an estimated misidentification error rate of a plurality of barcodes, the system comprising: a storage memory for storing a dataset associated with the plurality of barcodes, wherein the barcodes are selected to maximize the edit distance of each barcode relative to the other barcodes in the plurality of barcodes, and a processor communicatively coupled to the storage memory for determining, by a computer processor, the estimated misidentification error rates of the plurality of barcodes by performing simulated sequencing reads for each barcode and calculating, for each barcode, the fraction of simulated reads for which one or more other barcodes in the plurality of barcodes has edit distance less than or equal to that for the barcode from which the simulated read was generated.

In a seventh aspect, the present invention provides a computer-readable storage medium storing computer-executable program code, the program code comprising: program code for storing a dataset associated with the plurality of barcodes, wherein the barcodes are selected to maximize the edit distance of each barcode relative to the other barcodes in the plurality of barcodes, and program code for determining the estimated misidentification error rates of the plurality of barcodes by performing simulated sequencing reads for each barcode and calculating, for each barcode, the fraction of simulated reads for which one or more other barcodes in the plurality of barcodes has edit distance less than or equal to that for the barcode from which the simulated read was generated.

In various embodiments of the aspects above, the aspects further comprise filtering the first dataset to remove one or more barcodes whose sequences have a G:C content below a predetermined threshold value.

In various embodiments of the aspects above, the aspects further comprise filtering the first dataset to remove one or more barcodes capable of forming a hairpin structure.

In various embodiments of the aspects above, the aspects further comprise filtering the first dataset to remove one or more barcodes whose sequences include a known restriction site.

In various embodiments of the aspects above, the aspects further comprise filtering the first dataset to remove one or more barcodes whose sequences include a start codon.

In various embodiments of the aspects above, the aspects further comprise filtering the first dataset to remove one or more barcodes whose sequences include greater than three nucleotides in a row from the group consisting of A and T.

In various embodiments of the aspects above, the aspects further comprise filtering the first dataset to remove one or more barcodes whose sequences include greater than three nucleotides in a row from the group consisting of G and C.

In various embodiments of the aspects above, the aspects further comprise filtering the first dataset to remove one or more barcodes whose sequences include a homopolymer run greater than or equal to 2 nucleotides in length.

In various embodiments of the aspects above, the aspects further comprise filtering the first dataset to remove one or more barcodes whose sequences are complementary to an mRNA sequence in an organism.

In various embodiments of the aspects above, the aspects further comprise filtering the first dataset to remove one or more barcodes whose sequences are complementary to a genomic sequence in an organism.

In various embodiments of the aspects above, each barcode is from 5 to 40 nucleotides in length.

In various embodiments of the aspects above, the plurality of barcodes comprise at least 8, 16, 48, 96, 384, 1,000, 10,000, 100,000, or 1,000,000 barcodes.

In various embodiments of the aspects above, obtaining the dataset comprises generating the plurality of barcodes using a minimum edit distance, wherein the edit distance of each barcode relative to every other barcode is greater than the minimum edit distance.

In various embodiments of the aspects above, obtaining the first dataset comprises receiving the dataset from a third party.

In various embodiments of the aspects above, the simulated sequencing reads comprise zero or more sequencing errors that mimic the sequencing errors of a sequencing technology of interest.

In various embodiments of the aspects above, the sequencing technology of interest is 454 sequencing, SMRT sequencing, or Sanger sequencing.

In various embodiments of the aspects above, the sequencing errors comprise one or more substitutions, insertions, or deletions in the sequence.

In various embodiments of the aspects above, the estimated misidentification error rate is less than a desired worst-case misidentification error rate of 5%, 1%, 0.1%, or 0.01%.

In various embodiments of the aspects above, the estimated misidentification error rate is the average error rate of the individual barcode error rates.

In various embodiments of the aspects above, the estimated misidentification error rate is the maximum error rate of the individual barcode error rates.

In various embodiments of the aspects above, the estimated misidentification error rate is a specific percentile error rate of the individual barcode error rates, which can be the 50th percentile.

In various embodiments of the aspects above, the aspect further comprises selecting the plurality of barcodes for use in labeling one or more samples, wherein the selection is based upon the determined, estimated misidentification error rate of the plurality of barcodes being less than a desired misidentification error rate.

In various embodiments of the aspects above, the aspect further comprises selecting the plurality of barcodes for use in labeling one or more samples, wherein the selection is based upon the determined, estimated misidentification error rate of the plurality of barcodes.

In various embodiments of the aspects above, the aspect further comprises using the plurality of barcodes to label a plurality of samples, wherein each barcode is used to label a distinct sample.

In various embodiments of the aspects above, the plurality of samples is a plurality of B cell samples.

In various embodiments of the aspects above, the plurality of samples comprises B cells.

In various embodiments of the aspects above, the invention provides a plurality of barcodes generated by any of the aspects above.

In various embodiments of the aspects above, the plurality of barcodes can comprise at least 8, 16, 48, 96, 384, 1,000, 10,000, 100,000, or 1,000,000 barcodes.

In an eighth aspect, the present invention provides a plurality of barcodes for use in multiplex DNA sequencing, in which the plurality of barcodes has an estimated worse case misidentification error rate of less than 5%, 1%, 0.1%, or 0.01%, which can be generated by the aspects above. In various embodiments of this aspect, the plurality of barcodes comprises at least 8, 16, 48, 96, 384, 1,000, 10,000, 100,000, or 1,000,000 barcodes.

In an ninth aspect, the present invention provides a barcode for use in multiplex DNA sequencing comprising one or more of the sequences shown in Table 1 or Table 2.

In an tenth aspect, the present invention provides a method of barcoding a plurality of samples containing polynucleotide sequences of interest, said method comprising: (a) distributing the samples into a plurality of containers; (b) synthesizing polynucleotide sequences of interest using templates derived from the sample; and (c) adding a barcode sequence to the polynucleotide sequences of interest synthesized in step (b), wherein said barcode sequence comprises one or more of the sequences generated by the method of claim 1, 2, or 3.

In an eleventh aspect, the present invention provides a method of barcoding a plurality of samples containing polynucleotide sequences of interest, said method comprising: (a) distributing the samples into a plurality of containers; (b) synthesizing polynucleotide sequences of interest using templates derived from the sample; and (c) adding a barcode sequence to the polynucleotide sequences of interest synthesized in step (b), wherein said barcode sequence comprises one or more of the sequences shown in Table 1 or Table 2.

In a twelfth aspect, the present invention provides a method of increasing the accuracy of sequencing of a region of a nucleic acid sequence, comprising the steps of adding a barcode to a nucleic acid sample proximal to the region of interest and using the barcode to align a sufficient number of raw reads of the region of interest, such that the consensus sequence derived from the alignment has fewer indels and substitutions than the average single raw read.

In various embodiments of this aspect, the consensus sequence has at least fewer than half of the indel and substitution errors of the average single raw read.

In other embodiments of this aspect, the consensus sequence is formed from at least 10 reads and has fewer than 90% of the indel and substitution errors of a single raw read.

BRIEF DESCRIPTION OF THE DRAWINGS

These and other features, aspects, and advantages of the present invention will become better understood with regard to the following description, and accompanying drawings, which are provided as non-limiting illustrative examples of various aspects and embodiments.

DETAILED DESCRIPTION

Overview of Barcode Selection

DNA barcodes are sequences incorporated into DNA molecules and can be used to identify the sample from which the DNA was taken. Incorporating a distinct barcode for each of many samples allows for the pooling and parallel processing of the samples. We disclose herein sets of barcode sequences and methods for generating sets of barcode sequences useful for such sample multiplexing in DNA sequencing. The sets are designed to have an estimated worst-case sample misidentification error rate below a chosen threshold. Different sets of barcodes are tailored for specific sequencing platforms and the number of samples to be processed in parallel.

Figure 1:
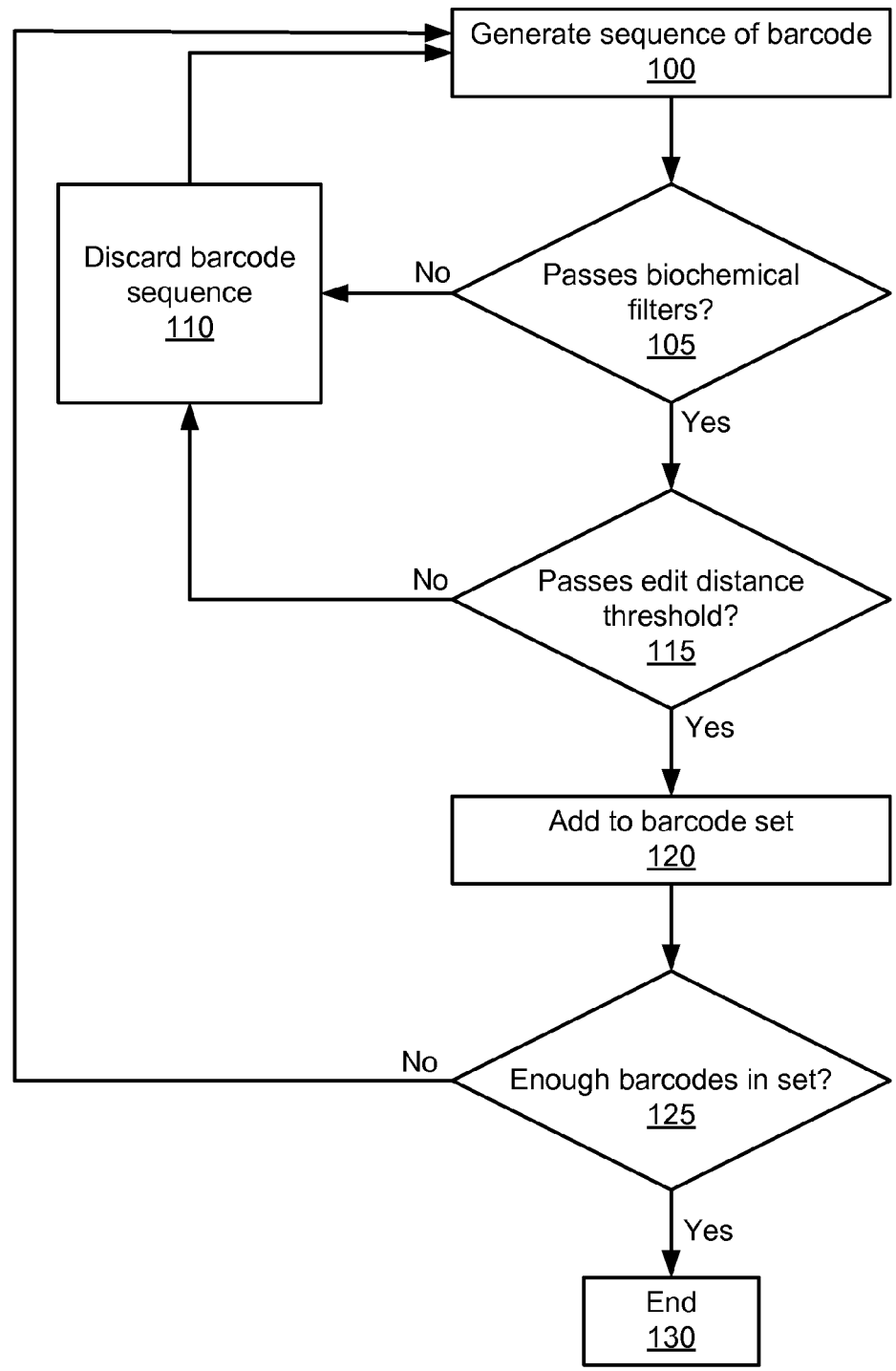
FIG. 1 is a schematic flow chart of a method for generating an initial set of barcode sequences for use with a specific sequencing platform, prior to determining estimated misidentification error rates.
Figure 2:
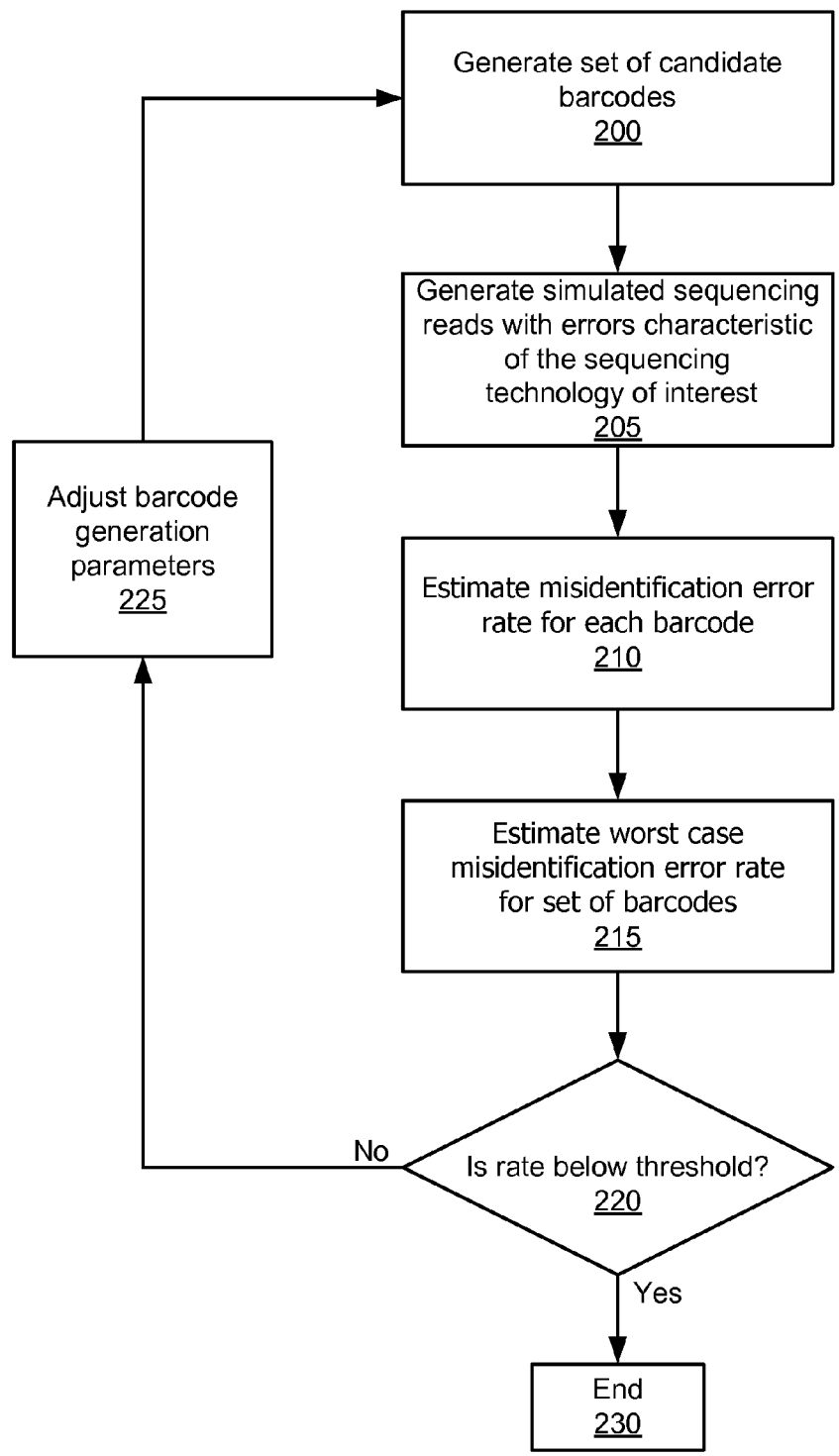
FIG. 2 shows a schematic flow chart of a method for generating a set of barcode sequences with an acceptably low estimated misidentification error rate for use with a specific sequencing platform.

In one embodiment, we disclose a method of designing barcodes that relies on generating an initial set of barcodes using one of a number of methods available in the art. For example, an initial set of barcodes can be designed to maximize sequence dissimilarity among members of the set, using a parameter such as edit distance. As described in greater detail herein, the barcodes in the initial set can then be tested in simulated sequencing runs, where the simulation takes into account the type and frequency of sequencing errors that arise using different sequencing platforms. Barcode sequences which are difficult to distinguish from other barcodes in the set based on the types of errors introduced into the simulated sequences by a particular sequencing platform can be eliminated from the set of barcodes. Additional barcodes can be designed and tested by the simulation methods disclosed herein and then included or excluded from the set of barcodes. FIGS. 1 and 2 provide schematic flow charts illustrating non-limiting examples of embodiments of the present invention to aid the reader in following the descriptions herein.

Definitions

In general, terms used in the claims and the specification are intended to be construed as having the plain meaning understood by a person of ordinary skill in the art. Certain terms are defined below to provide additional clarity. In case of conflict between the plain meaning and the provided definitions, the provided definitions are to be used.

As used herein, a "dataset" is a set of data associated with a barcode or set of barcodes. Such data can include physical characteristics of a barcode or set of barcodes, such as primary sequence, homology to other sequences, melting temperature, GC content, propensity to form a hairpin, among other distinguishing characteristics or parameters. A dataset may be determined experimentally, calculated, or derived from information in other databases or publications.

As used herein, the term "edit distance" refers to the minimum number of insertions, deletions or substitutions required to transform one sequence of nucleotides into a second sequence of nucleotides (Gusfield, Dan, "Algorithms on Strings, Trees and Sequences—Computer Science and Computational Biology", Cambridge University Press, 1997, pp 215-216).

As used herein, the term alignment refers to the identification of regions of similarity in a pair of sequences. For example, barcode sequences can be aligned, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), among others.

As used herein, a simulated sequencing read refers to a sequence of nucleotides generated by taking a given sequence of nucleotides, and randomly introducing insertions, deletions or substitutions into the given sequence, where the pattern of randomly introduced insertions, deletions or substitutions will typically mimic the known pattern of errors introduced by a particular sequencing technology.

As used herein, a misidentification error rate refers to the rate at which a barcode sequence fails to be uniquely and correctly identified from either real sequencing reads or simulated sequencing reads.

As used herein, an "estimated" error rate refers to the probability of error determined by calculation based on an error model or by sampling from simulation results based on an error model.

As used herein, a "worst case" as used in connection with a sample misidentification rate or performance refers to the highest overall estimated error rate for a given set of barcodes with a particular pattern of errors, where the pattern of errors is typically mimicking those of a given sequencing technology.

As used herein, an indel refers to an insertion or a deletion of one or more nucleotides within a particular sequence (such as a read) relative to another sequence (such as a barcode).

Characteristics of Barcode Sequences

Various sets of barcodes have been reported in the literature. Several researchers have used sets that satisfy the conditions imposed by a Hamming Code [Hamming, R. W., Bell System Technical Journal v. XXIX no. 2, pp. 147-160, April 1950, Hamady et. al. (2008), Nature Methods v. 5 no. 3, pp 235-237, Lefrancois et. al. (2009), BMC Genomics v. 10 no. 37 pp 1-18]. Others have used sets that satisfy more complex conditions than a Hamming Code but share the similar guarantee of a certain minimal pairwise Hamming distance [Fierer et. al. (2008), PNAS v. 105 no. 46 pp 17994-17999, Krishnan et. al. (2011), Electronics Letters v. 47 no. 4 pp. 236-237]. Such barcodes are not useful with a sequence that has an insertion or deletion in the region including the barcode. As an alternative to Hamming-distance based barcodes, others have selected sets of barcodes which satisfy a minimum pairwise edit distance. Sets of such barcodes can work with insertion, deletion or substitution errors in the read of a barcode sequence. However, none of the sets of barcodes reported in the literature have generally provided a useful expectance of performance, in the sense of estimated worst-case sample misidentification rates when used with a given sequencing technology. At best, these authors report a limited set of experimental results describing misidentification error rates for a small number of conditions defined by parameters such as number of samples, sequencing technology and biochemical processing steps in the production of barcoded DNA molecules.

We set out to solve the problem of designing sets of barcodes that would give well-defined worst-case performance in the presence of the types of errors seen with different sequencing techniques, such as, for example, a high rate of insertion and deletion errors, as might be seen in raw reads from the Pacific Biosciences Single Molecule Real Time (or SMRT) instruments, and for different numbers of samples processed in parallel. We also required sets of barcodes that satisfied certain biochemical properties. Some of our barcode sets satisfy these needs, and we have other sets of barcodes that satisfy other requirements in terms of desired worst-case performance, error rates of the sequencing technology, number of samples, and other biochemical constraints.

Examples of sequencing technologies relevant to the present invention include: classic dideoxy sequencing reactions (Sanger method), and NextGen sequencing platforms, such as sequencing by synthesis using reversibly terminated labeled nucleotides, pyrosequencing, 454 sequencing, allele specific hybridization to a library of labeled oligonucleotide probes, sequencing by synthesis using allele specific hybridization to a library of labeled clones that is followed by ligation real time monitoring of the incorporation of labeled nucleotides during a polymerization step, polony sequencing, single molecule real time sequencing, and SOLiD sequencing.

The sets of barcodes that we describe here are typically suitable for a certain sequencing technology. No DNA sequencing technology has perfect fidelity, so that when a DNA sequence is "read", there will be sequencing errors, and the sequencing errors are characteristic of the sequencing technology used. These sequencing errors can lead to the misidentification of a barcode sequence, i.e., where the actual barcode sequence being read is incorrectly identified as a different barcode. Because the characteristic sequencing errors vary from technology to technology, the estimated performance of a particular set of barcodes will vary by technology. If a given technology has a generally lower sequencing error rate than the technology for which a set of barcodes is "suitable", the performance of the barcode set will be superior. The estimated worst-case performance of the set of barcodes can be determined from the characteristic errors of the sequencing technology and analysis. If a given technology has a generally higher sequencing error rate than the technology for which a set of barcodes is "suitable", the performance of the barcode set will be inferior. The estimated worst-case performance of the set of barcodes can again be determined from the characteristic errors of the sequencing technology and analysis.

In one embodiment, the specific properties that various barcode sets satisfy include, but are not limited to, the following.

Every barcode in a set is unique, that is, any two barcodes chosen out of a given set will differ in at least one nucleotide position. Each set includes at least one unique barcode for each sample desired to be processed in parallel, and preferably no more. For example, if in a given instance it is desired to process 8, 16, 48, 96, 384 or more samples in parallel, then the corresponding set of barcodes will include at least 8, 16, 48, 96, 384 or more barcodes, but preferably exactly 8, 16, 48, 96, 384 or more barcodes. If it is not known how many samples will be processed in parallel, but if an upper limit on the number of samples that will be processed is known, then the set of barcodes will have at least as many barcodes as the upper limit on the number of samples, with preferably no more than that upper limit. For example, if the maximum number of samples to be processed in parallel is 1536, then the set of barcodes will have at least 1536 barcodes, and preferably no more than 1536.

In some embodiments, the number of samples being processed can be at least 10, 100, 1000, 10,000, 100,000, 1,000,000, or more, with the corresponding number of barcodes being used.

Each barcode sequence in the set satisfies certain biochemical properties that depend on how the set will be used. For example, certain sets of barcodes incorporated into cDNAs that will be cloned into expression vectors might not have an "ATG" present in them, to avoid a spurious start to translation when the expression vector construct is transformed. Certain sets of barcodes that will be used as, or that are contained within sequences which will be used for, PCR primers might have melting temperatures in a specific range, for example 52-58° C. Certain sets of barcodes that are used in an RT-PCR reaction should not have complementary sequences to any sequence in the genome of a certain organism or set of organisms. A requirement for non-complementity helps to ensure that the use of a particular barcode sequence will not result in mispriming during molecular biological manipulations requiring primers, such as reverse transcription or PCR. Certain sets satisfy other biochemical properties imposed by the requirements associated with the processing of the DNA molecules into which the barcodes are incorporated.

While avoiding any complementarity to sequences of an organism can be a filter, in some embodiments, one might instead eliminate complementarity just to sequences expressed in particular cells, tissues, or organs of a target organism, rather than the entire organism, if the use of the barcodes will be primarily with such subsets of a target organism.

An acceptable level of complementarity will vary depending on the needs of the experiment, and can, for example be less than 100%, 90%, 85%, 80%, 75%, 70%, 65%, 60%, 55%, 50%, 45%, 40%, 35%, 30%, 25%, 20%, 15%, 10%, 5%, or be 0%, and all values in between.

Complementarity can be determined using any of a number of well-known methods, for example, the algorithms incorporated into the NBLAST and XBLAST programs (version 2.0) as described in Altschul et al., Nucleic Acids Res. 25:389-3402 (1997).

In one embodiment, complementary barcode sequences are determined by a BLAST (Altschul, S. F., Gish, W., Miller, W., Myers, E. W. & Lipman, D. J. (1990) "Basic local alignment search tool." J. Mol. Biol. 215:403-410, Camacho C., Coulouris G., Avagyan V., Ma N., Papadopoulos J., Bealer K., & Madden T. L. (2008) "BLAST+: architecture and applications." BMC Bioinformatics 10:421) of barcode sequence against the human refseq mRNA database with blastn using default parameters except that the word_size parameter is set to 6. Any barcodes with a matching high scoring pair with score >=40, where the last nucleotide of the barcode sequence in the HSP is within 5 nucleotides of the 3' end of the barcode sequence, or where the overall length of the HSP is >=25 is considered a match. If the barcode sequence consists of multiple barcodes made up of a plate, universal primer and sample barcode, then in one embodiment complementarity is determined by a blastn match of the concatenated plate and universal primer sequences with an intervening spacer, or the concatenated universal primer and sample barcode sequence with an intervening spacer.

Each set of barcodes has a certain worst-case estimated performance. The worst-case estimated performance depends on the sequencing technology. In some cases, the worst-case estimated performance is determined by the maximum probability over all barcodes that a barcode will be misidentified as some other barcode in the set. In some cases the probability that a particular barcode will be misread as another barcode is not known exactly for the sequencing platform, so it is based on an estimate of the behavior of the platform when reading sequences similar to the particular barcode.

Each individual barcode has a certain probability or rate that it will be misidentified as some other barcode. In the practice of the present invention, any of a number of different metrics can be used to determine the estimated misidentification rate from the overall distribution of probabilities of misidentification. These include the average, the maximum, or a median or other percentile, and enumerated deviations from these metrics. In a preferred embodiment, the maximum error rate over all bar codes is used.

In one useful embodiment, some sets of barcodes useful for identifying which heavy and light chain cDNA sequences came from a particular single B cell out of a collection of B cells will preferably have worst-case estimated performance of fewer than 5% of barcodes misidentified.

When identifying which heavy and light chain cDNA sequences came from a particular single B cell out of a collection of, for example, 1760 B cells, with a sequencing platform having a 5% substitution error rate and a 15% insertion or deletion error rate, some sets of barcodes will have a minimum pairwise edit distance of 12.

In another embodiment, when identifying which heavy and light chain cDNA sequences came from a particular single B cell out of a collection of, for example, 1760 B cells, with a sequencing platform having a 1% substitution error rate and a 1% insertion or deletion error rate, some sets of barcodes will have a minimum pairwise edit distance of 5. Since all known sequencing technologies can only read a finite length of DNA, the lengths of the barcodes in each set are short, to maximize the amount of non-barcode sequence in each read. In some sets, which are suitable for identifying which heavy and light chain cDNA sequences came from a particular single B cell out of a collection of 1760 B cells, the barcodes include a sequence S1 followed by a sequence UP followed by a sequence S2, where the length of S1 is 28 nt, the length of S2 is 28 nt, the length of UP is 24 nt, and for any two barcodes in the set the edit distance between the respective S1 sequences is 12, the edit distance between the respective S2 sequences is 12, and the edit distance between the UP sequences is 0, and the estimated worst-case performance of the barcode set is a 5% misidentification error rate when the substitution error rate is 5% and the insertion or deletion error rate is 15%.

Optimized Barcode Design

As discussed above, one previously described approach for barcode design relies on generating oligonucleotides that are a certain Hamming distance (number of mismatches) apart, that follow an "error correcting" scheme such as a Hamming Code (see, e.g., Hamady et al. Nat. Method 5: 235-237, and http://en.wikipedia.org/wiki/Hamming_code). Hamming distance is a suitable measure of similarity only when indels are irrelevant. Also, using a Hamming Code restricts oligonucleotide sequences to those that satisfy the Hamming Code. This restriction in and of itself confers no additional benefit to identifying an oligonucleotide sequence from a read (in the sense that any set of sequences that have an equivalent Hamming distance apart are equally reliably delineated during sequencing), so the restriction simply limits the ability to choose oligonucleotide sequences that are suitable from, e.g., a biochemistry standpoint (such as lacking "ATG", minimal secondary structure, or having melting temperature in a desirable range). In any event, this approach does not explicitly account for the detailed error characteristics of a given sequencing platform when choosing a set of barcode sequences.

Another approach is to generate oligonucleotide sequences that are simply a certain edit distance (minimum number of mismatches, insertions and/or deletions) apart (see e.g., Qiu et al., Plant Phys. 133: 475-481 (2003)). These are superior to the Hamming code barcodes since they are robust to indels. However, these methods also do not explicitly account for the detailed error characteristics of a given sequencing platform when choosing a set of barcode sequences.

As disclosed herein, the present invention provides an approach to designing barcode tags that results in a higher success rate for correctly identifying the associated sample for a given sequencing platform. Specifically, we have developed a method for optimizing the design of the barcode sequences for a given sequencing technology taking into account the particular estimated set of errors associated with that sequencing technology.

More particularly, we provide a method for generating barcode sequences useful for sample multiplexing in DNA sequencing that are designed to have an estimated sample misidentification error rate below a chosen threshold.

As indicated above, due to the lack of perfect fidelity in any sequencing platform, when a DNA sequence is "read", there will be errors that are characteristic of the sequencing platform. These sequencing errors can lead to the misidentification of a barcode sequence, where the actual barcode sequence being read is incorrectly identified as a different barcode. The barcode sequences disclosed herein satisfy the property that the probability of incorrectly identifying a barcode from a sequencing read is below a prespecified, desired misidentification error rate threshold r. In particular, the design of our barcodes takes into account both the characteristic sequencing errors of a particular sequencing platform, as well as any characteristics of the algorithm used to identify a barcode from a sequence read that could lead to misassignment, for example the choice of a particular alignment scoring matrix.

In one embodiment, we design our barcodes to ensure that the minimum pairwise edit distance (Gusfield, Dan, "Algorithms on Strings, Trees and Sequences—Computer Science and Computational Biology", Cambridge University Press, 1997, pp 215-216) between any two barcodes is greater than or equal to a certain threshold d. We also require that our barcodes satisfy certain sequence restrictions that we call "filters". To actually generate a set of possible barcodes, we randomly generate one sequence at a time, verify that it passes the filters, and compare it to all previously generated barcode sequences to verify that the edit distance criterion is satisfied. The set of barcodes is then checked to verify that the probability of incorrectly identifying a barcode from a sequencing read is below an error rate threshold r.

The filters will vary depending on the samples that the barcodes will be used with. A suitable set of filters for a library of immunoglobulin heavy and light chain pairs prepared from individual cells might include, but are not limited to:

1. No ATGs
2. Not greater than 3 As/Ts or 3 Gs/Cs in a row (ATTG acceptable, ATTA not acceptable)
3. GC content between 40% and 60%
4. No homopolymer runs greater than or equal to 2 nt in length
5. No TCTG anywhere in sequence
6. Minimal secondary structure on DNA structure prediction
7. BLAST confirmation of no complementary sequence in the transcribed sequences of the target organism The check on misidentification error rate is done by simulating reads according to the characteristic sequencing errors associated with a particular sequencing platform. If a platform's error profile is not understood well enough or is difficult to model, it can be desirable to simulate poorer fidelity than the sequencing platform actually has. For example, it could be desirable to simulate an overall indel rate of 5% if it is known that the underlying technology has an average indel rate of 3% but that it can be up to 5% for certain types of sequence. The simulated reads are then analyzed using the barcode assignment algorithm that will be applied to the real sequences. If the misidentification error rate threshold is not satisfied then a suitable adjustment is made to the parameters used to generate the barcode sequences (for example, a larger value for d, a greater barcode length, or a smaller number of barcodes) and another set of barcodes is generated. The process is repeated until a set of barcodes with a satisfactory error rate is generated.

Simulations and Determination of Misidentification Rates

Reads are simulated for a specific platform: the one that will be used for sequencing. The simulation depends on the platform because different platforms have different performance. For example, Pacific Bioscience's SMRT sequencing technology has a fairly high error rate for insertion/deletion errors, where the sequencer incorrectly adds a nucleotide to, or incorrectly removes a nucleotide from, the actual sequence. This rate is in the 15-20% range. The 454 platform, by contrast, performs much better. Both 454 and Pac Bio have difficulty with homopolymer runs—if, for example, a sequence has 4 A's in a row, both platforms have a tendency to report fewer or greater than 4 A's.

An important aspect of the present approach is that the simulated reads take such platform idiosyncrasies into account, mimicking as closely as possible what one would see with actual reads. In this way, a useful prediction can be made of how well a given barcode will perform without needing to do one or more real sequencing runs.

More specifically, for example, as a measure of the accuracy of a simulation method, if one simulates 1000 reads of a given sequence and generates 1000 actual reads of the given sequence from a particular sequencing platform, the two sets of 1000 sequences should be indistinguishable if the predicted misidentification rate is to be accurate. This doesn't necessarily require that the two sets of sequences are identical, only that the types and frequencies of sequencing errors are indistinguishable in the two sets.

However, in practice one can't model perfectly because any particular sequencing technology may not be perfectly characterized and may have variation from run to run or with different preparation protocols, etc. In practice, one generally makes conservative simulations, where the assumed performance of the platform is no better than the worst case scenario one anticipated, given what is known about the platform, the samples and preparation protocols, and so forth.

In one embodiment, reads can be simulated by assuming an overall rate for substitutions and insertions/deletions, and then the sequence can be "mutated" nucleotide by nucleotide according to those error rates.

As an example, we can determine individual misidentification error rates by counting the number of simulated barcode reads that are misidentified as follows: (1) Take a known barcode; (2) Generate a simulated read, i.e. make a copy of the barcode sequence that has the same sorts of sequencing errors the sequencing platform would cause. (3) Then, analyze that simulated read to see which barcode in the overall set is "nearest" in terms of edit distance. If the "nearest" barcode was the original barcode that was used to simulate the read, then the correct identification has been made. If not, or if there is more than one "nearest" barcode, the barcode has been misidentified. This is repeated for each barcode until one is confident of what the estimated misidentification error rate is going to be for each barcode in the set.

The number of repetitions needed is determined by counting statistics. The simulations are like tossing coins or rolling dice in that the misidentifications are governed by a binomial distribution. As a hypothetical, suppose that a very large number of simulations for a read, maybe a billion, are run, and that it is found that 10 million times the barcode was misidentified. Then one could be very confident that for the simulated errors, the misidentification rate is very nearly 1%. Suppose instead that, with the exact same simulation conditions, one generated a relatively small number of simulated reads, say 100. Then there is an approximately 26% chance that one will see 2 or more misidentified reads in the simulation (even though it is known from the billion read simulation that the error rate is 1%).

To actually compute how many simulated reads one should generate, one needs to have an acceptable misidentification rate chosen (e.g., 5%), and then decide how confidently one wants to estimate the misidentification rate. Given a barcode with n simulated reads for which the barcode was misidentified for k of the simulated reads, the probability that the actual simulated misidentification rate is greater than threshold $r_0$, is given by $p=I_{r_0}(1+k, n-k)$, where $I_x(a,b)$ is the incomplete beta function (Abramowitz and Stegun, "Handbook of Mathematical Functions",U.S. Government Printing Office, Washington, D.C., 1972, Formula 6.6.1). For example, if an acceptable misidentification error rate is 5%, and a simulation shows that, for a particular barcode, 6 times out of 300 the barcode is misidentified, corresponding to 2%, the probability that the barcode's actual misidentification rate would be greater than 5% is approximately 0.005. Therefore it is highly likely that the barcode satisfies the acceptable misidentification error rate requirement, given the simulation.

The estimated misidentification rate for a given barcode is the fraction of simulated reads that are misidentified. If one simulated 1000 reads for a particular barcode, and 15 of those simulated reads are closer in edit distance to some other barcode, then the estimated misidentification rate is 1.5%.

In various embodiments, one can generalize the procedure to accommodate the use of multiple barcodes, for example, a plate ID and a well ID barcode separated by a universal primer sequence with a 3' adaptor sequence. A set of plate barcodes and a set of well barcodes are generated according to the procedure for sequences that will incorporate single barcodes but excluding the simulation step. A set of combined plate, universal primer and well sequences are created by concatenating together each combination of plate and well barcodes separated by the universal primer, with the adaptor at the 3' end, and with an intervening spacer between each of the plate, universal primer, well and adaptor sequences, where the spacers are introduced to prevent filter failures that might be caused by concatenation. For the filters listed above and a universal primer sequence of "CAACAACAACGAAGGAAGGGAAC", a suitable plate to universal primer spacer could be chosen by adding a "T" to the end of the plate barcode if it ends in "C", "A", or "G", and an "A" otherwise. A suitable universal primer to well spacer could be chosen by adding an "A" to the beginning of the well barcode if it starts with "G", "C", or "T", and a "T" otherwise. For an adaptor with sequence "AGGAGGG" a suitable spacer could be "T" if the well barcode ends in "C", "A", or "G", and "C" otherwise. Spacers can be chosen to avoid any potential homopolymer runs of greater than or equal to 2 nucleotides in length. For example, a plate ID barcode ending in "C" will create a "CC" homopolymer run when concatenated with the universal primer sequence, which starts with "C". It may not always be necessary to include a spacer to satisfy filter constraints, but adding one ensures that all multiple-barcode sequences are the same length, which could be desirable. Regardless of spacer choice, the multiple-barcode sequences can be required to satisfy a set of filters, for example the set of filters listed above.

In one embodiment, a cDNA library can be constructed with the following configuration of elements, e.g., for NextGen sequencing using the 454 platform: 454 titanium primer—plate barcode sequence—single nucleotide spacer—universal primer sequence—single nucleotide spacer—sample barcode sequence—single nucleotide spacer—adaptor sequence (for template switching). In this embodiment, the 454 titanium primer sequence comprises "CGTATCGCCTCCCTCGCGCCATCAG", the universal primer sequence comprises the universal primer sequence disclosed above, the adaptor sequence comprises the sequence disclosed above, the spacers are chosen according to the guidance provided above, and the plate and sample barcode codes are derived using the methods disclosed herein, and can include the sequences shown in Tables 1 and 2.

Once a set of concatenated multi-barcode candidates are created, reads are simulated, and the simulated sequences analyzed in the same way as disclosed above. The process iterates until a set of multi-barcode sequences with an acceptable misidentification error rate is generated.

It will be appreciated that alternative embodiments are encompassed by the present invention. For example, in one embodiment, a different alignment weight matrix can be used in analyzing the simulated sequences.

In another embodiment, a variety of sequencing error models may be used. Since any error model will be approximate, it is appropriate to assess a range of possible error models. For example, a hypothetical sequencing platform might have an overall average rate of 5% substitutions and 10% indels. In such instances, for robust design of barcodes, it may be desirable to simulate substitution rates up to 7% and indel rates up to 12%.

In a further embodiment, rather than using a uniform threshold distance d and adjusting it upwards if unable to achieve a particular misidentification error threshold, one can generate as many barcodes as possible that satisfy the threshold and misidentification error rate, then keep that set of barcodes and decrease d, adding barcodes when they satisfy the relaxed d constraint and overall error rate. One can continue relaxing d whenever necessary.

Computer Implementation

In one embodiment, a computer comprises at least one processor coupled to a chipset. Also coupled to the chipset are a memory, a storage device, a keyboard, a graphics adapter, a pointing device, and a network adapter. A display is coupled to the graphics adapter. In one embodiment, the functionality of the chipset is provided by a memory controller hub and an I/O controller hub. In another embodiment, the memory is coupled directly to the processor instead of the chipset.

The storage device is any device capable of holding data, like a hard drive, compact disk read-only memory (CD-ROM), DVD, or a solid-state memory device. The memory holds instructions and data used by the processor. The pointing device may be a mouse, track ball, or other type of pointing device, and is used in combination with the keyboard to input data into the computer system. The graphics adapter displays images and other information on the display. The network adapter couples the computer system to a local or wide area network.

As is known in the art, a computer can have different and/or other components than those described previously. In addition, the computer can lack certain components. Moreover, the storage device can be local and/or remote from the computer (such as embodied within a storage area network (SAN)).

As is known in the art, the computer is adapted to execute computer program modules for providing functionality described herein. As used herein, the term "module" refers to computer program logic utilized to provide the specified functionality. Thus, a module can be implemented in hardware, firmware, and/or software. In one embodiment, program modules are stored on the storage device, loaded into the memory, and executed by the processor.

Embodiments of the entities described herein can include other and/or different modules than the ones described here. In addition, the functionality attributed to the modules can be performed by other or different modules in other embodiments. Moreover, this description occasionally omits the term "module" for purposes of clarity and convenience.

Accordingly, in various embodiments, the present invention provides computer implemented methods, computer systems, and computer-readable storage medium for optimized barcode selection as disclosed herein. For example, in one embodiment, the present invention provides a system for determining an estimated misidentification error rate of a plurality of barcodes, which comprises a storage memory for storing a dataset associated with a plurality of barcodes, which are selected to minimize the alignment score of each barcode relative to the other barcodes in the plurality of barcodes, where the alignment score is determined by choosing a scoring matrix and performing a global alignment of the first barcode with the second barcode, and a processor coupled to the storage memory for determining the estimated misidentification error rates of the plurality of barcodes by performing simulated sequencing reads for each barcode and calculating, for each barcode, the fraction of simulated reads for which one or more other barcodes in the plurality of barcodes has alignment score greater than or equal to that for the barcode from which the simulated read was generated. In another embodiment, the present invention also provides computer-readable storage medium for storing computer-executable program code for executing the optimized barcode selection methods disclosed herein.

Kits

The invention also provides kits for adding the barcodes of the present invention to nucleic acid samples of interest. For example, kits can contain barcodes derived by the methods of the present invention, such as those found in Tables 1 and 2. The kit can include reagents for sample isolation and synthesizing polynucleotides of interest using templates derived from the sample, as well as, reagents for adding the barcodes to the polynucleotides. The kit can also contain instructions and suitable packaging.

The following examples are for illustrative purposes and are not intended to limit the scope of the present invention.

EXAMPLES

Example 1

Barcode Design

The following steps describe the generation of a set of barcodes suitable for a particular application. Each application will have its own parameters including the number of barcodes required, the barcode length, the maximal acceptable misidentification error rate and the filters that should be applied to the barcode sequences (GC content, hairpin formation, undesired restriction sites etc.).

Each set is selected to maximize the edit distances between the barcodes. The edit distance between two barcodes is the total number of mismatches and gaps found in an optimal global alignment between them. Having higher edit distances makes the barcodes as different from one another as possible and reduces the misidentification error rate. However, it also means that fewer qualifying barcodes can be found so, for some combinations of maximal acceptable misidentification error rate, filters and barcode length, it may not be possible to find the desired number of qualifying barcodes.

First, an initial value is selected for the required edit distance. One way to do this is to set the required edit distance to the length of the desired barcodes, which is its highest possible value. This required edit distance will have to be reduced during the design process in order to generate enough barcodes for most applications, but starting it high helps to achieve the greatest possible edit distances and therefore lowest possible estimated rates of misidentification. Alternatively, the required edit distance can be set lower (e.g. at half the length of the desired barcodes) to reduce the computational resources required.

Next, a barcode sequence is generated. The sequence is tested to see whether it satisfies the filter criteria, to ensure that the barcode sequence is predicted to be suitable for use given biochemical process requirements. If the barcode sequence is judged biochemically unsuitable based on the biochemical requirements, it is discarded and a new sequence is generated.

Each sequence that passes the filter criteria is then tested to ensure that it is sufficiently different from other sequences already included in the set. The edit distance between the new sequence and each existing sequence in the set is determined by a global alignment. If, for each existing sequence, the observed edit distance exceeds or equals the minimum required edit distance then the new sequence is added to the set. Otherwise the sequence is discarded.

Sometimes no sequence satisfying the filters and required edit distance will be found. Since searching of random sequences could go on indefinitely, some stopping conditions are used to curtail the search. In one approach, once a certain number of sequences have been tested and discarded (e.g. 1,000), the search will stop. In another approach, the search will stop after a certain time elapses (e.g. 1 minute). Then, the required edit distance is decreased by 1. If it is still greater than zero, a new search for a barcode sequence meeting the filter and distance requirements can begin. If the required edit distance reaches zero, the design run fails and comes to an end.

Once a sequence satisfying the filters and required edit distance is found, it is added to the set. The process continues until the desired number of barcodes has been selected, or until the design run fails.

Once the run has been completed the barcodes are tested by determining the estimated misidentification rate. This is done by generating simulated sequence reads, incorporating sequence errors that mimic as accurately as possible the distribution of errors observed for the sequencing technology of interest. Then, an attempt is made to identify the correct barcode corresponding to each simulated read. The barcode or barcodes with lowest edit distance to the read are identified. If an incorrect barcode is found to have the minimum edit distance to the read (including in a tie with other barcodes), the barcode is considered misidentified.

The number of simulated reads for each barcode is chosen to be high enough to give sufficiently accurate results for the calculation of estimated misidentification error rate. For example, if the desired estimated misidentification error rate for each individual barcode is 1%, and given that the misidentification errors are approximately Poisson distributed, then with 100 simulated reads a barcode with an unacceptably high 2% misidentification error rate would have a 40% chance of being estimated to have an error rate less than or equal to 1%. However, with 1000 simulated reads the same barcode has only a 1% chance of incorrectly being predicted to have a misidentification error rate of 1% or less.

The overall estimated worst-case misidentification rate is chosen to be the maximum over all of the individual barcode misidentification error rates determined from simulation. If the estimated worst-case misidentification error rate exceeds the desired estimated worst-case misidentification rate, the design run is considered to have failed.

When a design run fails, a new run can be attempted with different parameters (number of barcodes, length and maximal error rate). Decreasing the number of barcodes, altering the filters, increasing the length or increasing the maximal misidentification error rate can all increase the probability of success. In case of a successful design run, the resulting barcodes are estimated to have satisfactory biochemical properties for the desired biochemical processing, and when DNA sequences containing the barcodes are read on the matching sequencing technology platform, the probability of mis-identifying a sample is estimated to be lower than the worst-case misidentification rate determined by simulation.

In the case where multiple barcodes will be used, for example a plate and well barcode separated by intervening sequence segments, the procedure can include estimation of the misidentification error rate for the entire sequence construct including barcodes and the intervening sequences used to join them.

In one embodiment, the above procedure can be represented algorithmically as below. Given a set of filters (e.g., GC content, hairpin formation, undesired restriction sites, among others) and a candidate barcode sequence s let F(s) be True if the sequence s satisfies the filter criteria, and False otherwise. For two sequences $s_1$ and $s_2$ let $d(s_1, s_2)$ be the edit distance (global alignment of $s_1$ with $s_2$ using a weight matrix with 0 for matches, −1 for mismatches and gaps, edit distance=negative of score). Let S represent a set of barcode sequences.

Then, given a desired acceptable error rate r in misidentification, choose N barcodes of length L as follows.
1. Choose an edit distance threshold L>d>0
2. Generate a sequence s of length L at random such that F(s)=True, let S={s}.
3. If |S|=N go to step 8
4. Randomly generate a new candidate barcode sequence s such that F(s)=True.
5. If $d(s, s_i)$<d for any $s_i \in S$, go back to step 4
6. S<−S U {s}.
7. Go to step 3.
8. Determine the misidentification error rate for the barcodes $s_i \in S$. If the error rate >=r, increase d by 1 and go to step 2.

The error rate in step 8 can be determined either by calculation or simulation based on the particular sequencing platform that will be used to sequence the barcoded samples. Specifically,
1. For each $s_i \in S$ generate a set of reads $\{r_{ij}\}$ based on the appropriate sequencing error model for a given sequencing platform.
2. For each $r_{ij}$ find a barcode $s_k$, where 1≤k≤N, that gives the minimum of $d(r_{ij}, s_k)$. If the minimum is not unique or if k<>i then $r_{ij}$ was misidentified. Otherwise, $r_{ij}$ was identified correctly.
3. Compute the fraction of reads misidentified and check if it is below the acceptable error rate.

The overall process will fail to terminate if the misidentification error rate is too stringent. To avoid this, the number of iterations should be limited, and the length L increased if the number of iterations is exceeded.

In the case where multiple barcodes are used, for example a plate and well barcode separated by a universal primer sequence with a 3' adaptor, the procedure is as follows.
1. Generate a set of plate barcodes according to steps 1-7 above.
2. Generate a set of well barcodes according to steps 1-7 above.
3. Create a set of multiple-barcode sequences by concatenating plate, universal primer, well and adaptor sequences together, with appropriate spacers to enable the concatenated sequences to pass the filters.
4. Determine the misidentification error rate for the multiple-barcode sequences. If the error rate >=r, increase d by 1 and go to step 2.

Example 2

Exemplary Barcodes

We have used the approach to design a set of barcodes as shown below. The barcodes have been tested to determine which ones are suitable for barcoding cDNAs via template switching-mediated tailing of cDNA with a barcode-containing oligonucleotide during reverse transcription. This is just one of many possible applications. The subset of barcodes can be useful in a full-scale experiment which will include generation of paired heavy and light chain antibody sequences from a collection of single B cells. The barcode sequences shown below can be used singly or in various combinations, for example, to form sample and plate identifiers as discussed herein. For example, the sequences shown below can be used as sample barcodes.

TABLE 1

| Barcode Number | Barcode Sequences |
| --- | --- |
| 1. | GCGACGTCTGCTATCTCAGTGTGCAGTC |
| 2. | AGTCAGCGTGAGAGTACGTGCGTGTCAT |
| 3. | ACGACTGTGATCTGTGAGTACATCACGC |
| 4. | GCTATCGACAGTACTATCACAGTCAGCT |
| 5. | GCAGTCTCTATCGAGCGTACTCAGTACA |
| 6. | TAGAGTGTATCAGCTGACTGCGTCTATC |
| 7. | TCTGCAGACGTCGACTCTGCTGAGTGAC |
| 8. | ACATCTACTCGACACACTGTACAGTAGC |
| 9. | CGAGTACTACGTGTGACTGATACACTGC |
| 10. | ACTCGAGTGTCGCTGCACGTACGTACGT |
| 11. | GTGATCGACGTACAGAGTGATACGAGCT |
| 12. | CAGTATCGCTAGCATACTAGTGCAGATA |
| 13. | ACGTGCTACAGAGAGTCTGCTCAGAGCA |
| 14. | GTCGAGAGCACTACTACAGAGTCGATCA |
| 15. | GAGAGTCTCTACACACGATACGTAGATC |
| 16. | CGTAGTCACAGTGTAGTCGAGTCATCAG |
| 17. | ACACATCATCTACGTAGCGAGAGAGTAC |

TABLE 1-continued

| Barcode Number | Barcode Sequences |
|---|---|
| 18. | ACTAGATCGCTGCACGCATAGATACTAG |
| 19. | ATCACTACGCATCGCATCAGTATCTACG |
| 20. | CTAGTGTAGAGTCACGAGATCTCAGCAG |
| 21. | ACACGTACTCAGTCATACAGAGCGAGCA |
| 22. | ACTCATAGCGATACGTGTGCGTCATACG |
| 23. | GCTCTGTGTGTCGATACTCAGTCTACTA |
| 24. | CTGAGACAGACGACTAGTACGAGAGCGT |
| 25. | CGACGATCACGAGAGCATCTACACGTGC |
| 26. | ATAGAGACTAGAGATAGCTCGCACTGAT |
| 27. | TACTCTCTGAGATACATCACGCTCGACG |
| 28. | CTGTGTACGTGACGCACTGCGAGAGATC |
| 29. | CACAGTACTACACGTAGCTCGATCGACT |
| 30. | ACACTGCATAGAGACACTCACATCTCGA |
| 31. | GCGAGTGCGTGTATCGCACAGAGTGTAG |
| 32. | ACGAGACGAGACTGCGTCTACGCTGCAT |
| 33. | GTACTAGCGTATCACTAGAGTGCTGCGT |
| 34. | CTGTGATCAGATCACTCGATCAGCTGCT |
| 35. | CATCTGAGCACATCGCATACGCTACGTA |
| 36. | GCTGTCTGCGTCGCAGAGTACGACAGAT |
| 37. | GAGAGAGATCGCACACACACTGCTGCAC |
| 38. | GACTGATCGCTGAGACGTGCTGACGAGA |
| 39. | TAGTCTGTACACTAGAGACGTACGCAGA |
| 40. | CGCATAGCAGTGAGTCGATACTACGCTC |
| 41. | AGAGAGTACAGCGACGAGTAGATCATCA |
| 42. | AGCAGAGCACGTCTATCTGTACTATCTG |
| 43. | CGTATCTCACAGTACTCAGATAGCGTCT |
| 44. | ACATCAGTGTGCTGTGCGATCGACACTG |
| 45. | GCACAGCATCTCGCTGTAGAGTACGCTA |
| 46. | GCGACTAGCTGAGCGATACTGTAGTGAT |
| 47. | TACATCTAGACGTGCGTGACACTACAGA |
| 48. | GTAGTCATCTGTGCTCGATCACTGAGAC |
| 49. | ATAGACACACATCTGCTCACTGTAGCTC |
| 50. | ACTGAGCAGAGCATCGACTAGTGTCAGA |
| 51. | TAGAGACACGTCAGACACGAGACAGTAG |
| 52. | AGCGAGCAGATAGAGCACTGAGTAGTGC |
| 53. | GTCTGATACTCATCTATCGCAGATAGTC |
| 54. | TCTACAGCACGTACTAGCGACTCACGAC |
| 55. | CGATAGTCTATCTAGACGTCACTCAGTG |

TABLE 1-continued

| Barcode Number | Barcode Sequences |
|---|---|
| 56. | GACGATAGCACTAGCTCTGTGAGCTGAC |
| 57. | TACGTACGAGTGAGTACGAGTCGCTAGC |
| 58. | AGTGCACGATACACACAGTGTACGCTAT |
| 59. | CAGCGAGAGCATCTGTCAGCATAGTCAC |
| 60. | CTACTGTCATCACTGCTACGACGCATAC |
| 61. | CTCACGCTGATCAGATAGAGACTAGCAC |
| 62. | GACTGCGAGTCGACGAGTACTACGTCTA |
| 63. | TCGAGTCACAGTACAGTGTCTCGCAGCG |
| 64. | TCTGCGATAGACGCTACACACGTCGAGA |
| 65. | CTCACATAGTAGACGACAGTCACGACTG |
| 66. | GTAGCTCGCATACACGTGCTGAGTCGCA |
| 67. | TCGCTCTCTCACGATACTGCGTCTGAGT |
| 68. | GAGCATAGTACGTGAGTAGCAGTCAGCG |
| 69. | GCAGACATACGCACTCGAGTCGACTACG |
| 70. | TCATCAGTGTGTAGCACTAGTCAGTGTG |
| 71. | AGCACAGCTACGCAGTACACTAGATAGC |
| 72. | TCTGACTAGAGTCAGAGCGTCTACATCT |
| 73. | TAGCAGTGAGACATCGCTAGACTGCTAC |
| 74. | TACACGATAGAGTCTATCTAGCAGAGAG |
| 75. | CACTGTGCGTGCGTGTATCTGTCACGTC |
| 76. | CGTGACTCTAGCTACGTCGAGTAGTCGA |
| 77. | GTCTAGCACTCTCACGCTCATACAGTGA |
| 78. | CTAGACGTGTGACGAGTCACTATCGCAC |
| 79. | TCGAGCATACGTCTAGACACACGTCGCT |
| 80. | CTATCGATCGAGAGCTGACGCATCAGTA |
| 81. | CGTGTCTCAGCGATCTACGCTGTGCTCA |
| 82. | GTGCTCATCTATCAGCGAGTAGCGACTC |
| 83. | TCTAGAGATACTGTGCAGTCTGTCTAGC |
| 84. | GTGATCAGATACATCTACTCTCAGTCAG |
| 85. | TCTGCGTCAGTGAGATCACGCTGCAGAG |
| 86. | GAGTGTAGACGCTACATCGAGAGTACTG |
| 87. | GAGACTCTGTGTGTGATCATCGAGAGTA |
| 88. | TAGTCTCATCTCTCATCAGAGTGTGCAT |
| 89. | GCGTGCGAGATAGCATCTCGAGCATCAT |
| 90. | CGTAGCACGTCTCTGACGCTGAGTGCTA |
| 91. | TCACGCTCACGTGCTCAGTGATCATACT |
| 92. | GACACTCACTGTGCAGATCTACAGCTAT |
| 93. | CTCGACATCGAGTGCGTGTGTACGTCTC |
| 94. | TCGCTGCTGCGATAGCACGAGAGAGACA |

TABLE 1-continued

| Barcode Number | Barcode Sequences |
|---|---|
| 95. | ATACTCAGTCGACGATCTCTCGCTGTGT |
| 96. | CAGTAGTAGAGCACAGATAGCGTCTCGC |
| 97. | CACTCTACTGTGAGCAGTAGCACGTCAC |
| 98. | GTGTACATAGCGTAGATACTGATCGACA |
| 99. | CACATAGTCTGCTGAGTGTAGCGTGTGC |
| 100. | CAGCGAGTGTAGTGACATACAGAGCTGC |
| 101. | TACACACTCGCACATCGCTGCGTGACGA |
| 102. | CTACAGTCGAGTCATCAGTGCGTACGTA |
| 103. | GCGTCATCGCAGTGTACACGCATACAGC |
| 104. | TAGATCGCTCTCACACGCACGACACGTC |
| 105. | CTATCGAGAGAGCACGTGTGTCTCGCTA |
| 106. | AGTCGATCGATAGCACATCGCTCGCATA |
| 107. | GTCACAGTAGAGAGTCGATCGAGATACA |
| 108. | CGACGTCAGATACACTACAGATCACATC |
| 109. | AGTGCTCTGTAGTCGACGATAGCGTGCG |
| 110. | ATCAGCGACAGCTGTACAGTGTACACTG |
| 111. | GCGACACACGACACTCACACATACGTGA |
| 112. | CGTGTGCTCAGCAGCGACATCATCGAGA |
| 113. | GAGCGACAGCTGACGCTCGAGTATCACT |
| 114. | TCTACGTACGATAGCACGCACACTACTC |
| 115. | TCATACATACAGTCACATCAGAGTACGC |
| 116. | ATCTCTGCGTCGACACGTGAGCATACAT |
| 117. | TATCTGACGCACGTGACGCTGTCGATAC |
| 118. | AGTCACTCACGTAGTCACTGTCTCAGCT |
| 119. | TACGAGACACACGCAGCAGTACATCACG |
| 120. | ATCTGTGAGCGTCTCAGTAGCGTAGTCT |
| 121. | ACACAGACGACAGCATAGTACTGCGAGT |
| 122. | ACTGCTCTGCTGTACGAGAGCATCTGTA |
| 123. | GCACGTCACGACGTCATACATCTACACG |
| 124. | GAGCGAGCATAGCTCAGTCTACGTACGC |
| 125. | GTGATCACGAGTGAGACACGCTGCGTGT |
| 126. | AGTCTCAGCGAGTCTGAGCGACGTGAGT |
| 127. | GAGTGTGCTAGAGCGAGATAGCAGCGTC |
| 128. | CAGTGACGTAGTGTCGAGACGTGAGTAT |
| 129. | TCTCACTATCTAGACGATCGAGCTGTAT |
| 130. | CTGCGAGAGATCAGACGTGACACAGACG |
| 131. | TCGCTACGCACACAGTGAGTCTATCTGA |
| 132. | CGTGTATCACGTCGCACGTACTCGACAC |
| 133. | TAGTCGAGTAGACAGCGTGTAGTCATAG |
| 134. | GTCATAGCGTGTCTCAGCACGACTAGAC |
| 135. | AGCTGTAGACTATCTATCTGTGAGACGA |
| 136. | ACGCAGACAGCACTAGCATCTCTATCGC |
| 137. | CGTGTGTGTAGTGATCTATCTCTAGTAC |
| 138. | GCTCTAGATCGCATCTGTGTGCTGTCGA |
| 139. | GCGAGTGTGACGTGTCTGATACTGATAG |
| 140. | TATCAGTGATCTCTGACGCTACACAGAT |
| 141. | CTCGCACATCATCATCACACTCTGCAGC |
| 142. | GTGCAGTGTGTCACGACGTCATAGTGCT |
| 143. | CACTCACTCTATCGACTCATACATCAGT |
| 144. | ACGTACAGTCACTCTGTCGATCGAGCGT |
| 145. | CGCATCTAGCACGCAGCACGCACTATCA |
| 146. | GACATACTGAGCGTACACACTAGTACTG |
| 147. | TCATAGACAGTCGAGTGCAGCACATCAT |
| 148. | AGACGAGCGTGTAGATAGACTATCACAT |
| 149. | GTAGTATCAGATACGTGTCGACGCTATC |
| 150. | TAGACACACGCTGTGTGCGATACACACT |
| 151. | ACGCACACAGAGAGTGACACGAGCAGAG |
| 152. | AGAGATAGTCGATCAGATCTACACAGCT |
| 153. | ACTGCGATCGACGTGAGTCGAGACACAC |
| 154. | GTATCTCTGTCACTGTACATACACGAGC |
| 155. | GTGTATCGCTGTCGATCAGAGCGAGTAG |
| 156. | ATCATCTGTCTGCGACGCTCTAGTCAGC |
| 157. | GTGTCTGATCGCTGTCAGATCGCATCGA |
| 158. | GTATCGCTCTGCTACGACTAGCTATCTA |
| 159. | GATAGCAGCACGCTCACGAGTCTAGCGA |
| 160. | GCAGTGATACTCAGCGTGAGCACGTAGC |
| 161. | CGATAGATCGACTGCGATCATAGAGCGA |
| 162. | ATCAGTACGCTCAGAGCGTGTGCGAGCT |
| 163. | GAGTCTAGTGCTAGTGCGACAGACGACG |
| 164. | CAGCAGCATACATCATAGCGTATCATCA |
| 165. | ATACAGATCATACGACGTGTGCTGTCTA |
| 166. | CGATAGTGTGCGTACACTGAGTACTATC |
| 167. | CATCTAGTGACTACACATACGACACACG |
| 168. | ATCTCATACGAGCGTCAGTGTATCGAGC |
| 169. | TAGTGTGCTACGATCAGTCTCTCGCTGT |
| 170. | GTGCATCTAGCATAGACATCTAGCATAC |
| 171. | CGTGCATAGCATAGTGTACAGACACGTA |

TABLE 1-continued

| Barcode Number | Barcode Sequences |
|---|---|
| 172. | TCTGACATCTACAGTGCTCTCAGCGAGA |
| 173. | TAGAGTGCTGTCTGTATCACACTACGCA |
| 174. | TATCTGCAGATCACAGATCACGTACTAC |
| 175. | ATACTAGCGTAGACTGCATACTAGACAG |
| 176. | CTACGTCTCGACGACACGCAGAGTCGAT |
| 177. | ACATACGCTGTACGTACTGCGTGTACTC |
| 178. | AGAGAGTGTATCTCAGTGTGAGTAGCAT |
| 179. | AGATAGTAGTGCAGCGTACGTGTCGATA |
| 180. | CAGCAGCTGAGTATCTCTATCATCTAGT |
| 181. | CTAGTCGATCTGACACTAGTCTGTACAC |
| 182. | GTGCGTAGCGACAGTGCTGACTGTAGAC |
| 183. | CAGAGTAGTCTGACGTAGATCTGCGATC |
| 184. | TACATAGTGCATACGAGACACACTGCAC |
| 185. | CTCTGCTACTGCTACGTGTAGACAGTAT |
| 186. | AGTGTGTGTATCGAGTACGTCTGACACG |
| 187. | TCGATCTGTCGAGAGTATCTCATCGCTG |
| 188. | AGCGTCTGTACAGATAGCATCGATCAGT |
| 189. | TAGTACATCAGCGACTGCTGCGACTGCA |
| 190. | CACTCAGCATACTCGACAGATCTGTGAG |
| 191. | CACGCAGCGTAGCGTAGTGTAGACTACG |
| 192. | AGATACAGTCTACTAGAGAGTGCTGACG |
| 193. | TCTCAGCGACACGATCACGTCGAGAGTC |
| 194. | TCAGATCTCGCAGACATACAGCATCGCA |
| 195. | CGCTCTCATAGATAGAGCGAGTCGCAGA |
| 196. | CTGTCTGCACGCATCGAGTGTAGTCTAT |
| 197. | GCTACACTATCTCTACGCACTATCTAGT |
| 198. | AGAGCTGCGATCGAGTACATAGAGCTAT |
| 199. | CTGAGCACTACGCACGACTCTCTGTGTC |
| 200. | GTGTGCGAGCATCTACACGACGTGCTGT |
| 201. | AGCATCTCTGTAGAGACACAGTGCGTCA |
| 202. | CTAGAGCTCTCGAGTGCACTGACTGACG |
| 203. | GATCACGTCATCGATCATCTGTACGTCA |
| 204. | ACATCGCACACTACAGCACATCGACATA |
| 205. | AGCACTATCTCTGTATCACACGCAGCGT |
| 206. | CTGACTACTCTGTGATCGCTAGACATAG |
| 207. | GTGAGACGAGTGCTGCGAGTGATAGTCA |
| 208. | AGTGATACTGAGAGCGTACGTCGATCGC |
| 209. | ATAGTACACGTGTGTGAGTGCTGTGATC |

TABLE 1-continued

| Barcode Number | Barcode Sequences |
|---|---|
| 210. | GTGCTGCACGTAGTGTACGTGTGTACGT |
| 211. | ATAGCTCTGCGACAGCACAGTGTGCGTG |
| 212. | CGTCTGTGTGAGCTACGCTCTGTGTGTG |
| 213. | CAGACTGACACGAGATAGCACAGAGATC |
| 214. | GTACGTGTCTCATACTACACATCACGTG |
| 215. | TCGATCATCTGTACTACTCTCGACATAC |
| 216. | AGAGCGACTGCTGCTCTGAGCGTAGATA |
| 217. | AGTCGACAGCGTGTCATACTATCTAGTG |
| 218. | GACGCACAGACGATCTGTCTAGTCAGTC |
| 219. | TACAGCGTGTGAGAGCGATAGAGAGTCT |
| 220. | GTGATCTAGCGTGTGTGTGCATAGCACG |
| 221. | TACACAGACGAGAGAGCTCACATACGCT |
| 222. | ATCACGCAGAGCTCGCTCTGACAGCGTA |
| 223. | TCACGTACACACTCTGTGCTGAGATCTG |
| 224. | GATACAGTGACTACGTCAGTCTCAGTAC |

In some embodiments, the barcodes disclosed herein can be used in combinations comprising one or more additional barcodes that can serve as plate and well barcodes, and/or comprising other sequence elements such as sequencing primer, universal primer, and adaptor sequences. Examples of further barcode sequences which can, for example, be used as plate identification barcodes in combination with the sequences of Table 1 are shown below in Table 2.

TABLE 2

| Barcode No. | Oligonucelotide Sequence |
|---|---|
| 1 | GACACGTGTCATAGAGTCTAGATCACTC |
| 2 | AGCTATCACATAGCTGAGCAGACGATCT |
| 3 | AGTAGATACAGAGCAGCAGCTATCTACT |
| 4 | CTGCGTCTGTGCTGTCTAGAGAGAGCTA |
| 5 | ACGATCACGATCGCTGCGTAGTGACGTG |
| 6 | GATACAGACTCTAGCGACGCAGTACACT |
| 7 | GCGTCGCACGAGTATCGATCTGCTCATC |
| 8 | AGCTCGACTACGACGCTAGCATCGCTAC |
| 9 | CATCATACACGTGATAGAGACTGCACGT |
| 10 | TACACTCATAGACTCACGCAGTAGCATC |
| 11 | TCAGTGAGTCGATCGAGCTGATCGAGTC |
| 12 | CGTGTGAGACTAGTGTGTACATAGAGTG |
| 13 | AGCTAGTACAGTCTACACTGCACGCTCA |
| 14 | ACTAGCTCAGAGCTAGCTGATCACGTGT |
| 15 | GTGTGTCACGAGACTAGAGAGACTCTGC |

TABLE 2-continued

| Barcode No. | Oligonucleotide Sequence |
|---|---|
| 16 | CTCGCTGACTCTGCTGCATACATCACTA |
| 17 | GTGTGCTCTCATCACGCTCTGTGAGACT |
| 18 | TATCTCGACTCAGCAGTGCACAGAGTGT |
| 19 | GCACAGTCATCTGCAGCACACGTGTCAG |
| 20 | ACAGACACTCTAGCTGACAGCTCAGAGA |
| 21 | CGCAGACAGCTCATCGACGACACACATA |
| 22 | CATAGTGATCGAGAGTGTGTGACACTGT |
| 23 | CTGAGCGTGACTGTCACATCGACTGTGA |
| 24 | TACTAGCACTCTGTACGTACGCTAGCTG |
| 25 | CTCTGCATAGTACTCTGTGTCTGCACAC |
| 26 | ATAGCGTCTACGCTGAGACTCGCTCATA |
| 27 | CAGAGACTCGAGCTGACGTACTCTCTCT |
| 28 | GACTCTCTACATCTCAGACATCTGTGTC |
| 29 | AGACTGCAGTACTAGCACGATCGCTAGT |
| 30 | TCTGTCACGCTAGTCTAGTACTGACTCA |
| 31 | CACGTAGCAGTCACGTACACGCACGTGT |
| 32 | CAGCAGTGATCTCGACACGCTGTGACTA |
| 33 | ACTAGCGTACGTGCATAGTGTAGAGCGA |
| 34 | GATAGTGCTGCAGCTCTGCATCGCTCTG |
| 35 | CTGTCGCTACTGTGACTACAGCAGCACG |
| 36 | CGTCTGAGTCATCTCGACGTGAGCATAC |
| 37 | AGTCATACTCGCTGACTACTCTGTGAGT |
| 38 | GCAGTACATCTGAGTACGCATACATCAC |
| 39 | CGTACGTACTGCTCGCAGCTACTACGAG |
| 40 | AGATACGTGCACTGTCTCAGAGACAGCT |
| 41 | GTCGCTAGTCACTGATCTAGCGACGCAG |
| 42 | AGTGTCTAGTAGACTCAGTACTCTCGAC |
| 43 | TATCACTGACAGCAGCAGTATCGCAGAC |
| 44 | CATCGCTACACGACTGTAGCACTCTCTG |
| 45 | GAGCAGCGAGATACACGCATCTGCTCGA |
| 46 | TACAGCTCTCAGTGTGTGTCAGTAGCGT |
| 47 | GAGTCATCAGCAGAGTGACAGTGTCTAT |
| 48 | AGCTGACTGTGAGTATCTCGCAGATCTC |
| 49 | AGTATCTACTCTGAGTGACGAGTAGAGC |
| 50 | GCATACTGTATCATCTCATCTACTGCAC |
| 51 | GAGACTACTCACATCTCACGTGATAGAG |
| 52 | TCGCTCTGAGTGATCTGCACTACGATCT |
| 53 | AGAGTGCGTGCGTCACACAGCTCAGAGT |
| 54 | CTGTCTACACTACTACTCTGCACACGAG |
| 55 | TCTAGCATAGTGACTGACGTGAGCATCA |
| 56 | TACGTGCTCAGATCTCTCAGTCGACAGA |
| 57 | CATACAGCTGAGATCAGTAGACGAGCTG |
| 58 | AGACTCTACTCTCACTCTCTGAGTGCTG |
| 59 | ACTAGACTGAGTGTGTACTCACGCATAC |
| 60 | CACTCACAGCTGCTATCAGCTACGTACA |
| 61 | TACTACTACTGCTGTGTCTATCTGCACG |
| 62 | AGCACGAGCGTCTGAGATCTCTGCAGTA |
| 63 | CGTCTCTGTCGACGAGAGCTGATAGTAT |
| 64 | GTGCACGTGAGTAGTGTAGCTGAGACTG |
| 65 | ACGATACGTCGCATACACTCATCAGTCA |
| 66 | GTACGACTCTGCGTAGCTGTGTGCTCAT |
| 67 | TCACTGTGCTACGTCTCAGCACAGACGA |
| 68 | CAGATCTGCTGATCTGATCTGCACGTAG |
| 69 | ACTGTGACTGCAGATAGAGTCGCAGCAG |
| 70 | ATACTGACTCTATCACATACTCAGACGC |
| 71 | TCGCAGTACTGCAGCAGAGAGATACGTC |
| 72 | GTCTAGAGTGCATAGACTGCTACACAGC |
| 73 | TCTGTGCAGTCAGACTGCTGATCTCTAG |
| 74 | CAGCTGCGTGTAGATCTGAGTGCTAGCG |
| 75 | ACTCGCTCTGCTCTGCTGTACTGATCAG |
| 76 | TAGTACTATCACAGCTCTGACAGCACAG |
| 77 | AGCTGTGCATCTGCGTGTGCGAGTGTGA |
| 78 | TCGACTGACTCTCATAGAGCTAGCTGTG |
| 79 | GTAGCAGACGAGACACATCAGTGACAGT |
| 80 | CATCGACGCATAGCGATCGATAGCTCTG |
| 81 | GATACTCACTAGTCACGTGCAGTGCTGA |
| 82 | CACATCAGACGCTCACAGAGAGACTCTA |
| 83 | ACGTGCGCACACGAGACGTGTAGTACA |
| 84 | CGCTGATACGTCACTAGTCTGACTCAGA |
| 85 | ACTGACTGCATACGTACGTACTGAGTGT |
| 86 | CTGCACAGTATCGCATAGCTGTGTGTAG |
| 87 | GCGAGCTCTCATCTCGACAGAGACTCAC |
| 88 | TCACTAGTAGCTCATACTACTAGAGCAC |
| 89 | CATACGTGCATCTGACGAGATAGTGTGC |
| 90 | CGCTGCGTCTGACTCACATCACACTACT |
| 91 | ATAGTGTGAGACTCGATCGCATCACATC |
| 92 | AGTATCGCTACAGAGATCTCATCTGTAG |

TABLE 2-continued

| Barcode No. | Oligonucelotide Sequence |
|---|---|
| 93 | GTAGATACGTCTCGCTAGTCACAGCATA |
| 94 | TAGCGTGTCGCTACTGCACGTGCTCACT |
| 95 | CGCACTGCTGCGTAGTAGTGCTCTCTAG |
| 96 | AGCAGTCGCTGAGCGTACACTCACTGTC |
| 97 | GACACGCTAGTCTGTCTCTGTGACATAG |
| 98 | ACTCTCACTGTACGTGTGTGTACTCTGC |
| 99 | GTGAGCTCTATCATAGTCTCGCTGCTCA |
| 100 | CACTGTGACACTGTAGCTGCAGAGTGCA |
| 101 | CGCATACACTGTCTGTGTACTCGCTGTA |
| 102 | TCGAGTGCGAGCTCTACGCATACGAGAC |
| 103 | ATCTCTGTGAGCTGAGTGAGATACTGCG |
| 104 | CGAGCTGTATCAGCAGAGTCTCGAGATA |
| 105 | GAGATAGACGCTGTACGTGTCTCATAGC |
| 106 | GATAGCGTAGTGTCTAGCTCAGCGTCTC |
| 107 | ATCTGACGTGACTGATAGTCATACGTGT |
| 108 | CGTAGAGCACAGTGTACTCTCTGAGACT |
| 109 | ATCTCAGTCTCTCGCTAGTCTCTCACTG |
| 110 | GTGCGTGAGTAGACTCTCACGCACTGTA |
| 111 | GTGCTACTAGCACTATCTAGCATAGTGT |
| 112 | GTCACGTCAGACTGCTATCACGTGCTCT |
| 113 | GCTCTCAGAGTGTAGTCTGTGAGAGCTC |
| 114 | CAGTGCGACTCACACTCAGAGCGTCTCT |
| 115 | GAGTGAGCTGTGTGACAGCGTCTGTACA |
| 116 | TCTCGAGCGTCTGTATCGCAGCATCTGC |
| 117 | GCATCGCAGTATCAGAGCTGCGACTGTG |
| 118 | GTAGAGAGATACAGTCTACTAGATCGCT |
| 119 | ACACTCGAGTGCACTACAGCTGTCTGCA |
| 120 | ACATACACGATAGCGTATCTCACTCTCA |
| 121 | CTGAGCGTCTAGCTCATCACATAGCACG |
| 122 | GACGATCTAGAGTCTGCATAGTAGCTAT |
| 123 | CTCACGTATCTGTAGACGTGAGTAGAGA |
| 124 | CTCTCTACAGAGTCGACTCACTCTAGCG |
| 125 | GATACACATAGCTGCTGATAGAGTGTCA |
| 126 | ATACGAGAGAGTACTCTCGCTGCTATCT |
| 127 | TCGATCGCTGCAGTGCGAGACTCTACTC |
| 128 | CTACACTCTCATACTGTGAGCAGACTGA |
| 129 | CTCACTCGCAGCTACGAGCTCTCAGTGA |
| 130 | GTCAGTAGTGCTGTACGTAGTGACTCGA |
| 131 | GAGCGTCTCGATCTGTGACGCTGTCTAG |
| 132 | GCTGCATACACAGCTCGCTATCTCGCAC |
| 133 | GCGAGCACATCAGTGATACATCAGATAG |
| 134 | GATCATCGAGTACTGCTGTATCAGACAT |
| 135 | TAGACTCACAGAGACGAGTACGTCTGTG |
| 136 | ACACGTGTCGACTCGACTGTGCTCTGAT |
| 137 | CTCTGTAGAGCGAGTATCATAGTCATAG |
| 138 | GACTAGCGAGCTGTGCTCTACTCTCTGA |
| 139 | TCGCTGCGTCTATCTGTGTGACAGCTCA |
| 140 | GTAGTGTCACGCACTCTCTGACATAGTA |
| 141 | CGAGAGAGCAGCTCTGAGTACGTGTACT |
| 142 | GACTGAGACGAGCACTGTGCGTAGCATC |
| 143 | TCGCTGTAGACGCAGTGACAGTGCAGCT |
| 144 | CGCTGTAGTCTACACAGCGTGTGTAGTC |
| 145 | GACTGCTGTATCGCTCATCAGCGATACA |
| 146 | GCTGTGTGCACTCTGCATACAGTGCGAC |
| 147 | TATCACGAGCAGTCTCAGTGCTGATCGC |
| 148 | TAGTGAGATCTCGCATAGTGAGCGAGCG |
| 149 | TACGTACGATCATACATACGTGTGTGAG |
| 150 | ACGACGCATACTACTGTCACGCACTCAC |
| 151 | ACTGTATCTAGTACGTGCACACGCTCAG |
| 152 | GTGTGACGTGCTCTACGTAGCTCTGCTC |
| 153 | CGACACTGAGTGCTACAGCTCATCACGT |
| 154 | CTGCATCATCTCAGAGAGCATACACTAG |
| 155 | AGCGAGTACGCTAGTGTCTCACATCGCA |
| 156 | CTGATACTGTGTCTCTCTGCTGATCTGA |
| 157 | AGCTAGTGTGTAGCAGCTCTCATACAGA |
| 158 | TCTCTCGAGACGAGAGATAGAGACGTGA |
| 159 | GAGAGACTGTGTAGTGTAGAGCACAGAC |
| 160 | AGTGTCATCAGTCGCAGCATCACTCTGT |
| 161 | GATAGAGCACGCAGTAGTAGTATCTGTG |
| 162 | ATAGCACGCAGAGAGATCACGCAGACT |
| 163 | CGTGTGTACTCAGTGTCATACTGCACAT |
| 164 | ACACTCGCATCAGTCAGAGTGATAGTCT |
| 165 | GCATACTAGAGCTCTCTGACATCTACAT |
| 166 | TATCGCACAGTGCGTACTCGATCTGACA |
| 167 | TCATCTACTCTGCGAGAGTCGCTCTACT |
| 168 | TCTACGTGTGCGACTCTACTCATAGT |
| 169 | GCAGATAGAGAGACGCATACTCTGTCTA |

TABLE 2 -continued

| Barcode No. | Oligonucelotide Sequence |
|---|---|
| 170 | AGCAGCTCGAGATACTAGTGAGCAGCAC |
| 171 | CGTGTGCGTCTGTGATAGTACAGTCTCT |
| 172 | TAGTGTGCAGTACACGCTATCAGTATCA |
| 173 | CGCACATCACGAGAGTGTGCTGTGTACA |
| 174 | GCGTCATAGCTGCTCGAGAGTCTGAGCA |
| 175 | GCTCAGAGCAGACGATCTGTCTCACGCT |
| 176 | TATCGACACAGCACAGAGAGAGACAC |

Example 3

Barcode Optimization for Use with the Pacific Biosciences SMRT Sequencing Platform The sets of barcodes above were designed for use with the Pacific Biosciences SMRT sequencing platform (Science 2 Jan. 2009: Vol. 323 no. 5910 pp. 133-138). The SMRT platform is characterized by long raw reads with relatively low substitution error rates, but fairly high indel error rates. It is also unique among sequencing platforms in that a circular DNA template can be read in a rolling circle fashion, resulting in multiple reads of each base in the template. The redundant read information can be used to generate what Pacific Biosciences refers to as a "Circular Consensus Sequence" (CCS), in which the base call error rate is much lower than that from a raw SMRT read. The barcodes were designed to give an estimated misidentification rate, based on simulation, of less than 10% with a substitution error rate of 5%, and an indel error rate of 15%. The error rates were chosen to be conservative relative to the estimated error rates from raw SMRT reads.

In order to test these barcodes, the barcodes are incorporated into a cDNA library of immunoglobulin lambda chains derived from PBMC mRNA using a template-switching reverse transcription method as described in PCT application No. PCT/US2012/000221, filed Apr. 27, 2012, and the library is sequenced using the SMRT platform. Of the resulting raw reads, a certain number will be of sufficient length and quality to produce CCS sequences.

Each of the CCS sequences and raw reads are analyzed to identify the most closely matching barcode based on edit distance by performing a standard global alignment to each possible barcode and its reverse complement. The barcode with the smallest edit distance is identified as the match for the read, with no match in case of a tie. An identical analysis is performed for the corresponding raw reads. A distribution of edit distances for CCS and raw reads is determined from this procedure. The mode, median and average of the edit distance for the raw reads is higher than the mode, median and average of the edit distance for the CCS reads since the CCS reads generally have a lower error rate.

The distribution of edit distances between reads and corresponding best-matching barcode is determined by a global alignment with matches scoring 0, mismatches, insertions and deletions scoring −1, no penalties for gaps at the beginning or end of a read sequence, and the negative of the alignment score giving the edit distance. Based on the distribution of edit distances and length of the barcodes, the basecall error rate is estimated for raw reads and CCS reads.

Under the assumption that all barcode assignments made with the CCS reads are correct, the accuracy of barcode assignment for raw reads is assessed. For each CCS read, the barcode is assigned based on edit distance. The number of CCS reads that have the same barcode assignment is the observed number of reads for that barcode. For each raw read from the set of CCS reads assigned to a particular barcode, a barcode is assigned by edit distance. Each instance where the barcode assigned to the raw read differs from the barcode of the CCS read is an observed barcode misidentification error. For each barcode, the sum of all observed barcode misidentification errors divided by the number of observed reads gives the observed misidentification error rate for that barcode.

For a well designed set of barcodes, it would be estimated that the observed misidentification error rate for all barcodes is either below the worst-case estimated misidentification error rate, or not statistically significantly above the worst-case estimated misidentification error rate. It will be understood by persons skilled in the relevant art that various changes in form and details can be made therein without departing from the spirit and scope of the various aspects of the invention.

Example 4

Use of Barcodes to Improve the Accuracy of Sequence Determinations from the Pacific Biosciences SMRT Sequencing Platform SMRT CCS reads have higher accuracy than the raw reads as each circularized DNA sequenced is read at least 3× and the concensus sequence obtained is of a higher quality than the raw reads. However, this is only applicable when the DNA sequence is of a length at least 3× shorter than the obtainable read length using SMRT technology. For example, for an amplicon of a read length of ~800 bp, if only 10% of SMRT reads are above 2.4 kb, then only 10% of all reads are usable to form CCS reads, as the rest of the reads are too short for a 3× coverage of the same DNA molecule, and the raw reads themselves are of too low a quality to be useful. Using barcodes to identify raw reads from a single sample of a particular amplicon allows for a consensus derived from at least 3 individual reads to give an accuracy equivalent to CCS reads. This also increases the number of useful sequences as now all raw reads of lengths 800 bp or greater are useable, which may be as high as 80-90% of all reads obtained. Therefore, as more reads are obtained, the cost per by is also lowered.

A set of barcodes is designed to have a worst-case estimated misidentification rate of approximately 5% when used to identify the barcodes from SMRT raw reads. The barcodes are incoporated into an amplicon library, where each barcode uniquely identifies each sample. Barcodes are incorporated via ligation or via PCR amplification where the barcode sequences are incorporated in the primers used. The library is then sequenced using the SMRT platform to an average coverage of at least 3× per cDNA.

The barcodes present in the raw reads are identified to determine groups of raw reads that come from the same sample. The raw reads from a single sample of a particular amplicon are assembled to produce a consensus sequence. In some embodiments, the consensus sequence derived from the assembly of at least 3 corresponding raw reads should have fewer than half of the indel errors of the average raw read. Alternatively, consensus sequences having at least 10 reads should have fewer than 90% of the indels of the raw reads.

Example 5

Use of Barcodes for Correction of Sequencing Errors from SMRT Sequencing of Highly Related Sequences, Such as SNPs A set of barcodes is designed to have a worst-case estimated misidentification rate of approximately 5% when used to identify the barcodes from SMRT raw reads. The barcodes are incoporated into a library focused on individual genomic regions, such as those selected using Nimblegen sequence capture technology. Rolling circle amplification is used to amplify genomic DNA, and Nimblegen sequence capture technology is used to enriched for individual genomic regions. Examples of specific genomic regions of interest are those containing single polymorphism nucleotides (SNPs), where deep sequencing is used to find SNPs in a population; other examples include highly conserved genomic DNA of microbial communities, where sequencing is used to identify the microbial species present in a sample based on differences in genomic sequence.

Barcodes are incorporated via ligation and each barcode uniquely identifies a specific genomic region of each sample. The library is then sequenced using SMRT platform to an average coverage of at least 3× per DNA segment.

The barcodes present in the raw reads are identified to determine groups of raw reads that come from the same sample. The raw reads from a single sample of a particular amplicon are assembled to produce a consensus sequence. In some embodiments, the consensus sequence derived from the assembly of at least 3 corresponding raw reads should have fewer than half of the indel errors of the average raw read. Alternatively, consensus sequences having at least 10 reads should have fewer than 90% of the indels of the raw reads.

Example 6

Use of Barcodes for Correction of Sequencing Errors from SMRT Sequencing of Immunoglobulin Gamma, Lambda or Kappa cDNA Sequences A set of barcodes is designed to have a worst-case estimated misidentification rate of approximately 5% when used to identify the barcodes from SMRT raw reads. The barcodes are incorporated into a cDNA library of immunoglobulin gamma, kappa or lambda chains derived from PBMC mRNA using a template-switching reverse transcription method as described in PCT application No. PCT/US2012/000221, filed Apr. 27, 2012, and the library is sequenced using the SMRT platform to an average coverage of 3× per cDNA.

The barcodes present in the raw reads are identified to determine groups of raw reads that come from the same well. The raw reads from a single well are assembled to produce a consensus sequence. In some embodiments, the consensus sequence derived from the assembly of at least 3 corresponding raw reads should have fewer than half of the indel errors of the average raw read. Alternatively, consensus sequences having at least 10 reads should have fewer than 90% of the indels of the raw reads.

Example 7

Use of Barcodes for Correction of Sequencing Errors from SMRT Sequencing of T Cell Receptor Alpha, Beta, Gamma or Delta cDNA Sequences A set of barcodes is designed to have a worst-case estimated misidentification rate of approximately 5% when used to identify the barcodes from SMRT raw reads. The barcodes are incorporated into a cDNA library of T cell receptor alpha, beta, gamma or delta chains derived from PBMC mRNA using a template-switching reverse transcription method as described in PCT application No. PCT/US2012/000221, filed Apr. 27, 2012, and the library is sequenced using the SMRT platform to an average coverage of 3× per cDNA.

The barcodes present in the raw reads are identified to determine groups of raw reads that come from the same well. The raw reads from a single well are assembled to produce a consensus sequence. In some embodiments, the consensus sequence derived from the assembly of at least 3 corresponding raw reads should have fewer than half of the indel errors of the average raw read. Alternatively, consensus sequences having at least 10 reads should have fewer than 90% of the indels of the raw reads.

It must be noted that, as used in the specification and the appended claims, the singular forms "a," "an" and "the" include plural referents unless the context clearly dictates otherwise.

All references, issued patents and patent applications cited within the body of the instant specification are hereby incorporated by reference in their entirety, for all purposes.

The invention claimed is:

1. A method for labeling a sample with a plurality of barcodes, comprising:
 obtaining a dataset, wherein the dataset comprises data associated with the plurality of barcodes, wherein the barcodes are selected to maximize the edit distance of each barcode relative to the other barcodes in the plurality of barcodes;
 determining, by a computer processor, the estimated misidentification error rates of the plurality of barcodes by performing simulated sequencing reads for each barcode and calculating, for each barcode, the fraction of simulated reads for which one or more other barcodes in the plurality of barcodes has edit distance less than or equal to that for the barcode from which the simulated read was generated;
 determining if the fraction of simulated reads of the barcodes in the dataset is below an error rate threshold; and
 labeling one or more samples with the barcodes having simulated reads below the error rate threshold.

2. The method of claim 1, further comprising removing from the plurality one or more barcodes with a G:C content above a predetermined threshold value.

3. The method of claim 1, further comprising removing from the plurality one or more barcodes whose sequences have a G:C content below a predetermined threshold value.

4. The method of claim 1, further comprising removing from the plurality one or more barcodes capable of forming a hairpin structure.

5. The method of claim 1, further comprising removing from the plurality one or more barcodes whose sequences include a known restriction site.

6. The method of claim 1, further comprising removing from the plurality one or more barcodes whose sequences include a start codon.

7. The method of claim 1, further comprising filtering the dataset to remove one or more barcodes whose sequences include a homopolymer run greater than or equal to 2 nucleotides in length.

8. The method of claim 1, further comprising removing from the plurality one or more barcodes whose sequences are complementary to an mRNA sequence in an organism.

9. The method of claim 1, further comprising removing from the plurality one or more barcodes whose sequences are complementary to a genomic sequence in an organism.

10. The method of claim 1, wherein each barcode is from 5 to 40 nucleotides in length.

11. The method of claim 1, wherein obtaining the dataset comprises generating the plurality of barcodes using a minimum edit distance, wherein the edit distance of each barcode relative to every other barcode is greater than or equal to the minimum edit distance.

12. The method of claim 1, wherein obtaining the dataset comprises receiving the dataset from a third party.

13. The method of claim 1, wherein the estimated misidentification error rate is less than a desired worst-case misidentification error rate of 5%, 1%, 0.1%, or 0.01%.

14. The method of claim 1, wherein the estimated misidentification error rate is the average error rate of the individual barcode error rates.

15. The method of claim 1, wherein the estimated misidentification error rate is the maximum error rate of the individual barcode error rates.

16. The method of claim 1, wherein the estimated misidentification error rate is a specific percentile error rate of the individual barcode error rates.

17. The method of claim 1, further comprising selecting the plurality of barcodes for labeling the one or more samples, wherein the selection is based upon the determined, estimated misidentification error rate of the plurality of barcodes.

18. The method of claim 1, further comprising labeling a plurality of samples with the barcodes, wherein each barcode is used to label a distinct sample.

19. A method for labeling a sample with a plurality of barcodes, comprising:
 determining, by a computer processor, the estimated misidentification error rates for a set of candidate barcodes by performing simulated sequencing reads for each barcode and calculating, for each barcode, the fraction of simulated reads for which one or more other barcodes in the set of candidate barcodes has edit distance less than or equal to that for the barcode from which the simulated read was generated;
 determining the plurality of barcodes whose estimated misidentification error rate of simulated reads of the barcodes is below an error rate threshold; and
 labeling one or more samples with the plurality of barcodes having simulated reads below the error rate threshold.

* * * * *